United States Patent
Kosuge et al.

(10) Patent No.: US 8,771,842 B2
(45) Date of Patent: Jul. 8, 2014

(54) BENZO[B]CHRYSENE COMPOUND AND ORGANIC LIGHT-EMITTING ELEMENT INCLUDING THE SAME

(75) Inventors: Tetsuya Kosuge, Yokohama (JP); Jun Kamatani, Tokyo (JP); Kengo Kishino, Tokyo (JP); Hiroyuki Tomono, Numazu (JP)

(73) Assignee: Canon Kabushiki Kaisha, Tokyo (JP)

(*) Notice: Subject to any disclaimer, the term of this patent is extended or adjusted under 35 U.S.C. 154(b) by 432 days.

(21) Appl. No.: 13/076,111

(22) Filed: Mar. 30, 2011

(65) Prior Publication Data
US 2011/0240974 A1 Oct. 6, 2011

(30) Foreign Application Priority Data
Mar. 31, 2010 (JP) ................................. 2010-082816

(51) Int. Cl.
*H01L 51/54* (2006.01)
*C07C 15/20* (2006.01)
*H01L 51/00* (2006.01)
*H01L 51/50* (2006.01)

(52) U.S. Cl.
CPC ............ *C07C 15/20* (2013.01); *H01L 51/0058* (2013.01); *H01L 51/006* (2013.01); *H01L 51/5012* (2013.01); *H01L 51/0056* (2013.01); *H01L 51/0055* (2013.01); *C07C 2103/52* (2013.01); *Y10S 428/917* (2013.01)
USPC ........... 428/690; 428/917; 313/504; 313/506; 585/26; 257/40

(58) Field of Classification Search
None
See application file for complete search history.

(56) References Cited

U.S. PATENT DOCUMENTS

| 7,183,010 B2 | 2/2007 | Jarikov | |
|---|---|---|---|
| 2004/0076853 A1* | 4/2004 | Jarikov | 428/690 |
| 2005/0134171 A1* | 6/2005 | Kobayashi | 313/504 |

FOREIGN PATENT DOCUMENTS

| JP | 2010-034456 A | | 2/2010 |
|---|---|---|---|
| JP | 2010-073989 | * | 4/2010 |
| JP | 2010-073989 A | | 4/2010 |

OTHER PUBLICATIONS

Translation for JP 2010-073989 (publication date Apr. 2010).*
J.Org.Chem.1980,45,1424-1428.

* cited by examiner

*Primary Examiner* — Dawn L. Garrett
(74) *Attorney, Agent, or Firm* — Canon U.S.A., Inc., IP Division

(57) ABSTRACT

The present invention provides a benzo[b]chrysene compound represented by general formula [1] below and an organic light-emitting element including the compound.

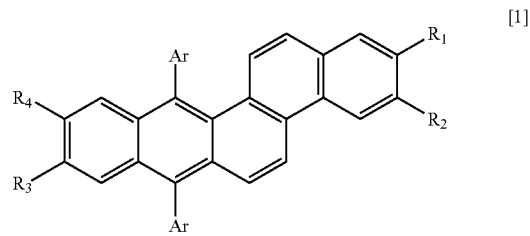

In the general formula [1], Ar represents a substituted or unsubstituted aromatic hydrocarbon group, and $R_1$ to $R_4$ are each independently selected from the group consisting of a hydrogen atom, substituted or unsubstituted alkyl groups, and substituted or unsubstituted aromatic hydrocarbon groups.

12 Claims, 1 Drawing Sheet

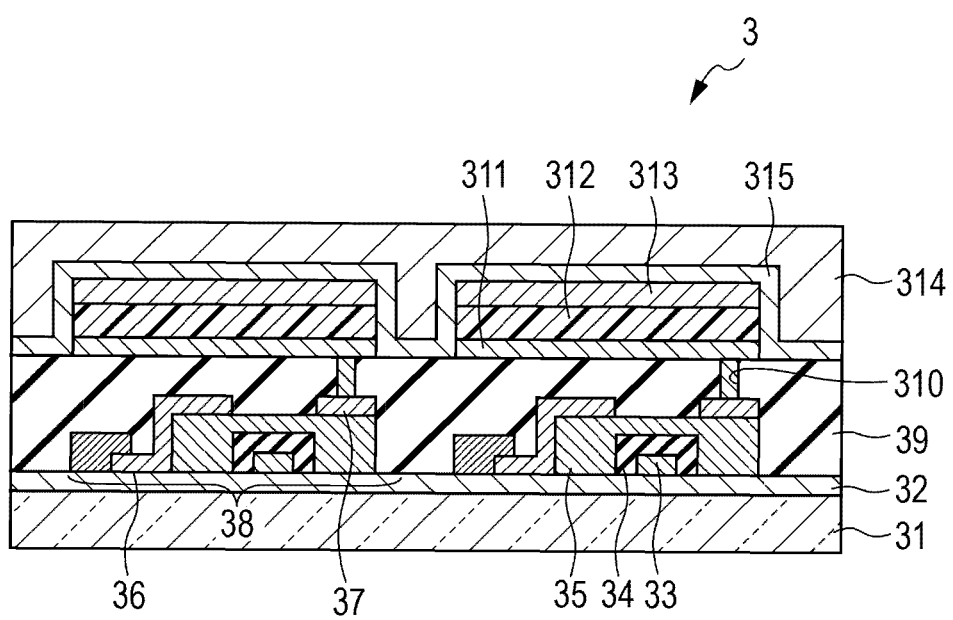

BENZO[B]CHRYSENE COMPOUND AND ORGANIC LIGHT-EMITTING ELEMENT INCLUDING THE SAME

BACKGROUND OF THE INVENTION

1. Field of the Invention

The present invention relates to a novel benzo[b]chrysene compound and an organic light-emitting element including the same.

2. Description of the Related Art

Organic light-emitting elements are widely investigated because they are expected to have high luminance with a low applied voltage, diversity of emission wavelengths, and high-speed response, and to thin and weight-lighten light-emitting devices.

Under the present situation, there is room to further improvement, and novel compounds are created as organic compounds possessed by organic light-emitting elements, particularly polycyclic aromatic hydrocarbons (PAH).

One of the polycyclic aromatic hydrocarbons is benzo[b]chrysene. U.S. Pat. No. 7,183,010 discloses 2,3-benzochrysene as compound 444 which is an unsubstituted benzo[b]chrysene as an example of associated compounds in organic light-emitting elements using excimer emission due to molecular association. A structural formula of benzo[b]chrysene is shown below.

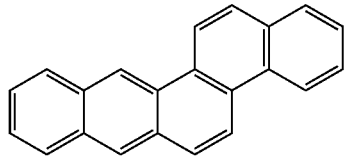 [SMILES: c1ccc2cc3c(ccc4c5ccccc5ccc34)cc2c1]

In addition, J. Org. Chem., 1980, 45, 1424 (p. 1427, lower right) discloses a method for synthesizing a benzo[b]chrysene compound having an aryl substituent only at the 5-position, i.e., 5-(2-naphthyl)benzo[b]chrysene, and physical property values thereof. A structural formula of the benzo[b]chrysene compound having an aryl substituent only at the 5-position is shown below.

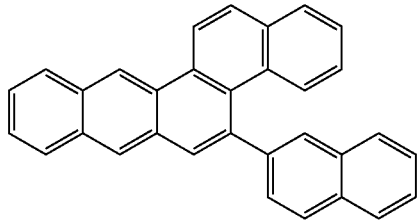 [SMILES: c1ccc2cc(-c3cc4cc5ccccc5cc4c4ccc5ccccc5c34)ccc2c1]

SUMMARY OF THE INVENTION

An object of the present invention is to provide a novel compound exhibiting satisfactory luminescence, more specifically a novel benzo[b]chrysene compound. Another object of the present invention is to provide an organic light-emitting device exhibiting high luminous efficiency and low drive voltage.

Accordingly, aspects of the present invention provides a benzo[b]chrysene compound represented by the following general formula [1]:

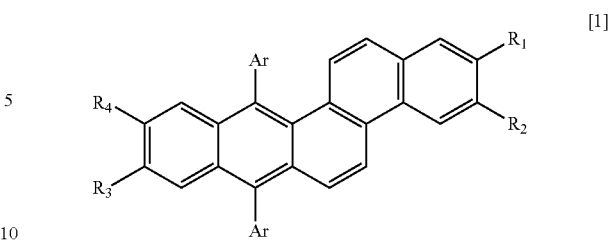

In the general formula [1], Ar represents a substituted or unsubstituted aromatic hydrocarbon group, and $R_1$ to $R_4$ are each independently selected from the group consisting of a hydrogen atom, substituted or unsubstituted alkyl groups, and substituted or unsubstituted aromatic hydrocarbon groups.

Further features of the present invention will become apparent from the following description of exemplary embodiments with reference to the attached drawing.

BRIEF DESCRIPTION OF THE DRAWINGS

FIGURE is a schematic sectional view showing an organic light-emitting element and a switching element connected to the organic light-emitting element.

DESCRIPTION OF THE EMBODIMENTS

Main Skeleton and Substituent of benzo[b]chrysene Compound According to an Aspect of the Present Invention Benzo[b]chrysene compounds according to aspects of the present invention are represented by the following general formula [1]:

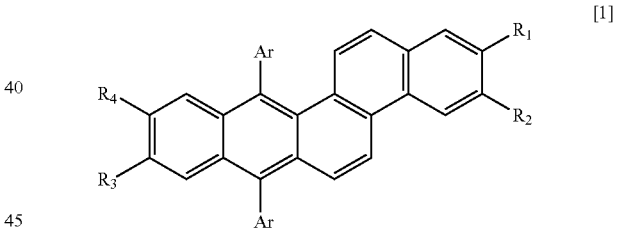

In the formula [1], Ar represents a substituted or unsubstituted aromatic hydrocarbon group.

Examples of an aromatic hydrocarbon group represented by Ar include a phenyl group, a naphthyl group, a phenanthryl group, a fluorenyl group, an anthracenyl group, a chrysenyl group, a pyrenyl group, a perylenyl group, an indenyl group, an acenaphthylenyl group, an acenaphthenyl group, a biphenylenyl group, a fluoranthenyl group, a benzofluoranthenyl group, a triphenylenyl group, and a naphthacenyl group.

Examples of substituents which may be further introduced to the aromatic hydrocarbon group include alkyl groups such as a methyl group, an ethyl group, a n-propyl group, an iso-propyl group, a tert-butyl group, a n-hexyl group, a cyclohexyl group, and the like; hydrocarbon aromatic groups such as a phenyl group, a tolyl group, a tert-butylphenyl group, a xylyl group, a mesityl group, a naphthyl group, a phenanthryl group, a fluorenyl group, a 9,9-dimethylfluorenyl group, a 9,9-diethylfluorenyl group, a 9,9-di-(n-hexyl)fluorenyl group, and the like; heteroaromatic groups such as a thienyl group, a benzothiophenyl group, a dibenzothiophenyl group, a pyrrolyl group, a pyridyl group, a triazyl group, a phenanthrolinyl group, and the like; substituted amino groups such as a dimethylamino group, a diethylamino group, a dibenzylamino group, a diphenylamino group, a ditolylamino group, a dinaphthylamino group, and the like; alkoxy groups such as a methoxy group, an ethoxy group, and the like; aryloxy groups such as a phenoxy group, a naphthoxy group, and the like; halogen atoms such as fluorine, chlorine, bromine, iodine, and the like; a hydroxyl group; a cyano group; and a nitro group.

In the formula [1], $R_1$ to $R_4$ are each independently selected from the group consisting of a hydrogen atom, substituted or unsubstituted alkyl groups, and substituted or unsubstituted aromatic hydrocarbon groups.

Examples of alkyl groups represented by $R_1$ to $R_4$ include a methyl group, an ethyl group, a n-propyl group, an iso-propyl group, a n-butyl group, an iso-butyl group, a sec-butyl group, a tert-butyl group, a n-pentyl group, a neopentyl group, a n-hexyl group, a n-octyl group, a n-decyl group, a n-dodecyl group, a cyclopropyl group, a cyclobutyl group, a cyclopentyl group, a cyclohexyl group, a norbornyl group, and an adamantyl group.

Examples of the aromatic hydrocarbon groups represented by $R_1$ to $R_4$ include the same as those described above for the aromatic hydrocarbon group represented by Ar in the formula [1].

Examples of substituents which may be further introduced to the alkyl groups and the aromatic hydrocarbon groups include the same as those described above for the aromatic hydrocarbon group represented by Ar in the formula [1].

In addition, in a benzo[b]chrysene compound represented by the formula [1], all or part of the hydrogen atoms thereof may be substituted by dueterium.

The benzo[b]chrysene compound represented by the formula [1] may be a compound represented by formula [2].

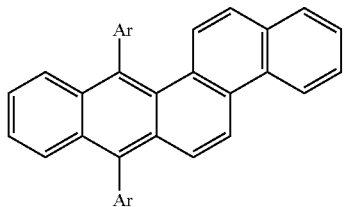

[2]

In the formula [2], substituent Ar is the same as Ar in the formula [1].

Further, the benzo[b]chrysene compound represented by the formula [2] may be a compound represented by formula [3].

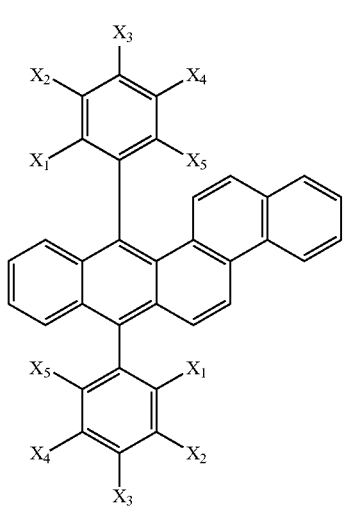

[3]

In the formula [3], $X_1$ to $X_5$ are each independently selected from the group consisting of a hydrogen atom, substituted or unsubstituted alkyl groups, and substituted or unsubstituted aromatic hydrocarbon groups.

Examples of alkyl groups represented by X1 to X5 include the same as those of alkyl groups represented by R1 to R4 in the formula [1]. Examples of substituents which may be further introduced to the alkyl groups include the same as those described above for the alkyl groups represented by R1 to R4 in the formula [1].

Examples of aromatic hydrocarbon groups represented by X1 to X5 include the same as those of the aromatic hydrocarbon group represented by Ar in the formula [1]. Examples of substituents which may be further introduced to the aromatic hydrocarbon groups include the same as those described above for the aromatic hydrocarbon group represented by Ar in the formula [1].

The benzo[b]chrysene compound according to aspects of the present invention is a compound having a benzo[b]chrysene ring as a main skeleton. The "main skeleton" refers to a skeleton which is positioned at a center of a molecular structure of the compound and which characterizes the physical properties of the compound. Namely, in the benzo[b]chrysene compound according to aspects of the present invention, the main skeleton refers to a skeleton irrelevant to the substituents as Ar and R1 to R4 in the formula [1].

(Properties of benzo[b]chrysene Compound According to Aspects of the Present Invention)

The benzo[b]chrysene compound according to aspects of the present invention is a compound having low S1 energy and shallow HOMO level (low ionization potential).

In each of a benzo[b]chrysene ring and an anthracene ring, substituent position Nos. are shown below.

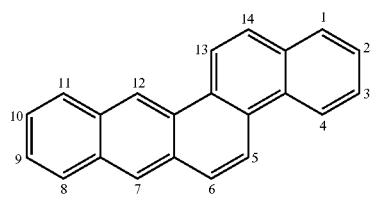

Benzo[b]chrysene

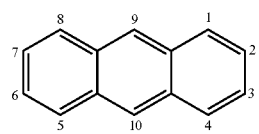

Anthracene

The benzo[b]chrysene ring contains a chrysene ring and an anthracene ring as partial structures in its skeleton. The benzo[b]chrysene compound having the benzo[b]chrysene ring as the main skeleton has lower S1 energy and shallower HOMO level than both a chrysene compound having the chrysene ring as a main skeleton and an anthracene compound having the anthracene ring as a main skeleton. This is described by comparison between the main skeletons of these compounds.

The results of molecular orbital calculation (B3LYP/6-31G*) of the S1 energies and HOMO levels of benzo[b]chrysene, chrysene, and anthracene are as shown in Table 1 below.

TABLE 1

| | Structural formula | S1 energy in terms of wavelength | HOMO level |
|---|---|---|---|
| Benzo[b]chrysene | 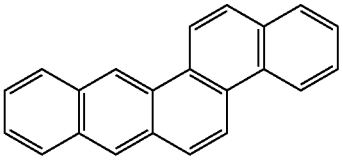 [SMILES: c1ccc2cc3c(ccc4c5ccccc5ccc34)cc2c1] | 395 nm | −5.19 eV |
| Chrysene | 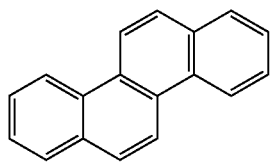 [SMILES: c1ccc2c(c1)ccc1c3ccccc3ccc21] | 328 nm | −5.51 eV |
| Anthracene | 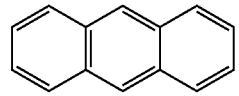 | 387 nm | −5.23 eV |

According to the results of calculation, the S1 energy of benzo[b]chrysene is lower than that of chrysene. This is because the benzo[b]chrysene ring has a larger π conjugate plane due to fusion of a benzene ring to a chrysene ring. For the same reason, S1 energy of benzo[b]chrysene is lower than that of anthracene due to fusion of a naphthalene ring to an anthracene ring in the benzo[b]chrysene ring.

Further, the results of calculation indicate that the HOMO level of benzo[b]chrysene is shallower than those of chrysene and anthracene. The term "shallower HOMO level" represents a small absolute value of HOMO level and a small difference between the vacuum level and the HOMO level, and also represents a low ionization potential of the compound. This is because the benzo[b]chrysene ring originally contains an anthracene ring having a shallow HOMO level. In addition, the shallower HOMO level than that of anthracene is possibly due to a specific structure of the benzo[b]chrysene ring in which a naphthalene ring is fused to an anthracene ring at the 2-position thereof.

Since the benzo[b]chrysene is reflected in a benzo[b]chrysene compound having a benzo[b]chrysene ring as a main skeleton, the benzo[b]chrysene compound is a compound having a shallow HOMO level and low S1 energy (small energy gap). In consideration of this point, the benzo[b]chrysene compound according to aspects of the present invention has been achieved.

However, the benzo[b]chrysene ring has very high planarity and thus unsubstituted benzo[b]chrysene exhibits significant intermolecular stacking. Therefore, for example, in view of use for an organic light-emitting element, as described below, direct use of an unsubstituted benzo[b]chrysene compound is considered to be unsuitable except for the purpose of positively utilizing intermolecular stacking as disclosed in U.S. Pat. No. 7,183,010.

Therefore, in the benzo[b]chrysene compound according to aspects of the present invention, aromatic hydrocarbon groups are provided at the 7- and 12-positions of benzo[b] chrysene. These substitution positions are positions each showing a particularly large dihedral angle, a substantially right angle, between the aromatic ring hydrocarbon substituent and the benzo[b]chrysene ring. Therefore, the aromatic hydrocarbon groups provided at the 7- and 12-positions become steric hindrance groups to intermolecular overlap of benzo[b]chrysene rings, and thus have the large effect of decreasing intermolecular stacking of the benzo[b]chrysene compound.

Further, the benzo[b]chrysene compound according to aspects of the present invention has high oxidation resistance and high chemical stability due to the aromatic hydrocarbon groups provided at the 7- and 12-positions of benzo[b]chrysene.

The 7- and 12-positions of benzo[b]chrysene are positions corresponding to the 9- and 10-positions of the anthracene skeleton, and thus carbon atoms at the 7- and 12-positions are very weak against oxidation. Therefore, in order to achieve chemical stability, it is necessary to cap the 7- and 12-positions with substituents. In this case, aromatic hydrocarbon groups, not alkyl groups or heteroaromatic groups, can be used as the substituents. This is because since charge distribution of HOMO and LUMO of the benzo[b]chrysene compound are present on the benzo[b]chrysene ring as the main skeleton, direct bonding of sp2 carbons of aromatic hydrocarbon groups to these positions is advantageous in terms of energy.

In addition, the benzo[b]chrysene compound according to aspects of the present invention has high conductivity of carriers of both the holes and electrons. This is because the benzo[b]chrysene main skeleton has transversely longer π conjugation than anthracene and chrysene, and thus good carrier conductivity can be expected.

The benzo[b]chrysene compound according to aspects of the present invention may have substituents at the 1-, 2-, 9-, and 10-positions of benzo[b]chrysene. When these positions are substituted by aromatic hydrocarbon groups, π conjugation of benzo[b]chrysene is further extended, and thus the S1 energy of the benzo[b]chrysene compound is further decreased. In addition, when these positions are substituted by alkyl groups, the HOMO level of the benzo[b]chrysene compound is further shallowed by the electron donating property of the alkyl groups. Namely, the S1 energy and HOMO level of the benzo[b]chrysene compound can be finely controlled by appropriately selecting the substituents at the 1-, 2-, 9-, and 10-positions of benzo[b]chrysene.

(Method for Synthesizing benzo[b]chrysene Compound According to Aspects of the Invention)

Next, a method for synthesizing the benzo[b]chrysene compound according to an embodiment of the present invention is described.

The benzo[b]chrysene compound according to an embodiment of the present invention can be synthesized by a synthesis route represented by the following formula [4].

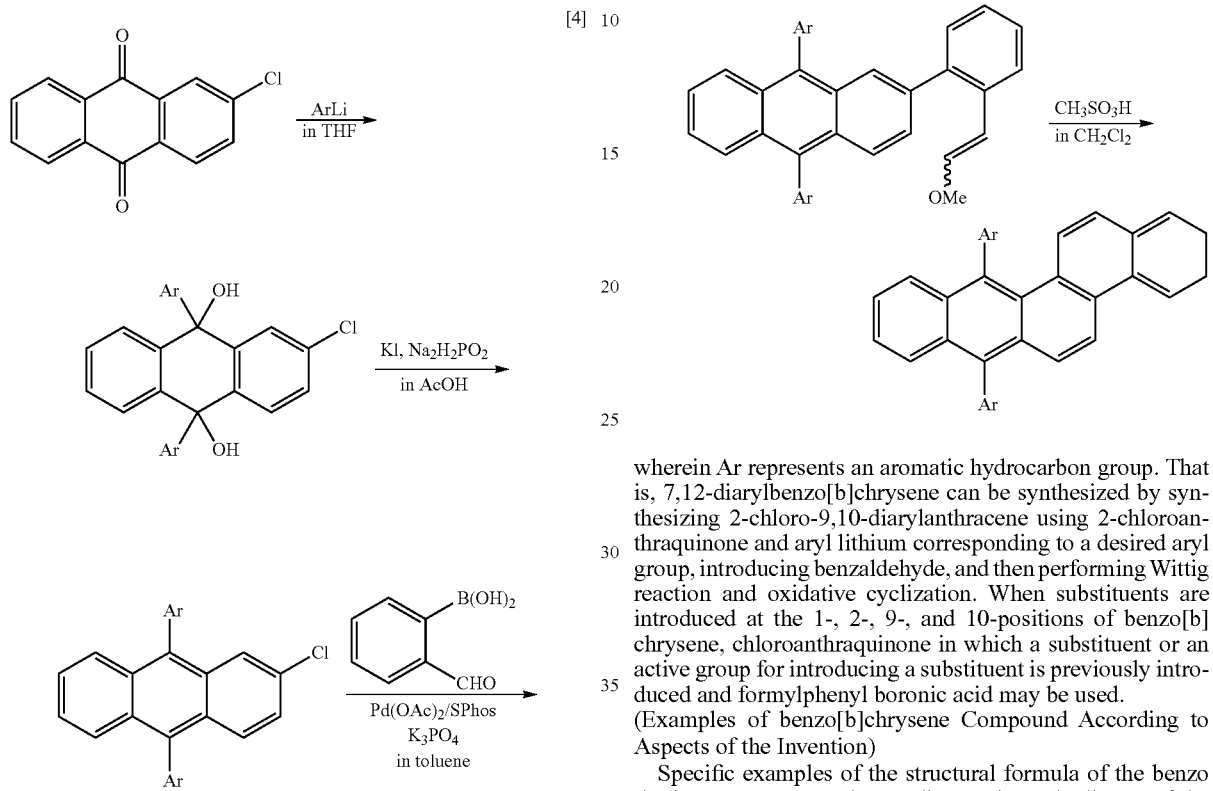

wherein Ar represents an aromatic hydrocarbon group. That is, 7,12-diarylbenzo[b]chrysene can be synthesized by synthesizing 2-chloro-9,10-diarylanthracene using 2-chloroanthraquinone and aryl lithium corresponding to a desired aryl group, introducing benzaldehyde, and then performing Wittig reaction and oxidative cyclization. When substituents are introduced at the 1-, 2-, 9-, and 10-positions of benzo[b]chrysene, chloroanthraquinone in which a substituent or an active group for introducing a substituent is previously introduced and formylphenyl boronic acid may be used.

(Examples of benzo[b]chrysene Compound According to Aspects of the Invention)

Specific examples of the structural formula of the benzo[b]chrysene compound according to the embodiment of the present invention are given below.

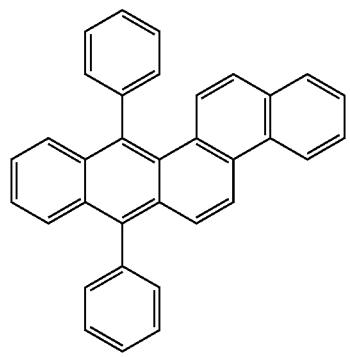

A01

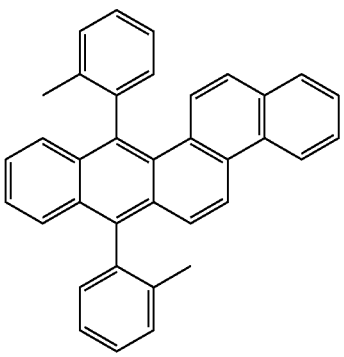

A02

-continued
A03
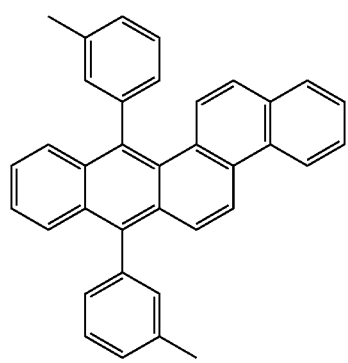
A04
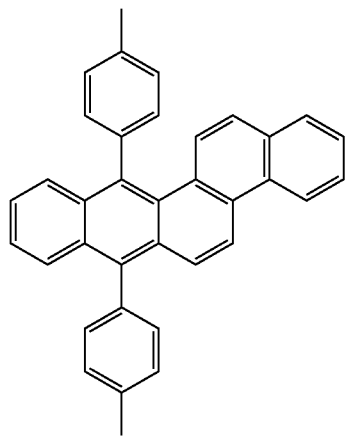
A05
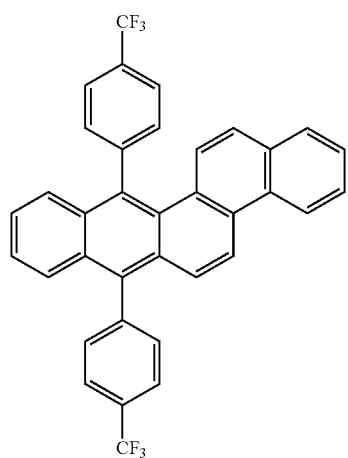
A06
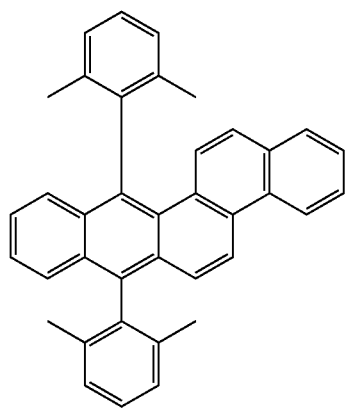
A07
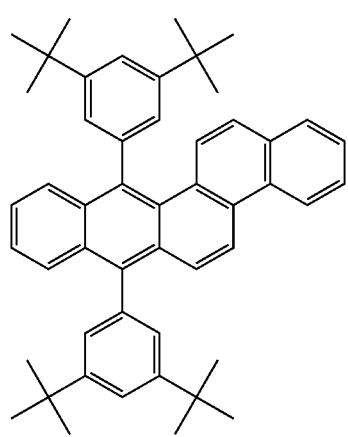
A08
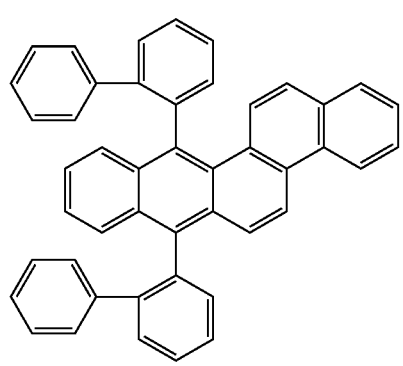

-continued
A09
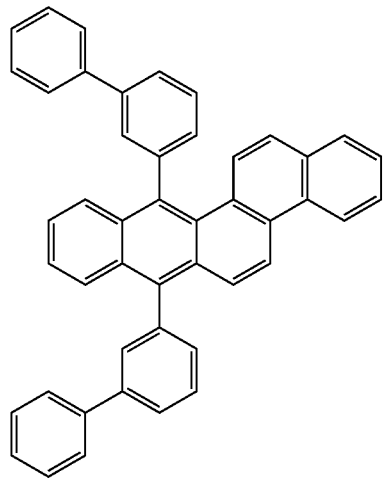
A10
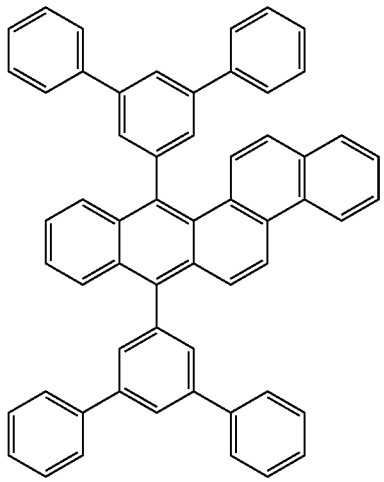
A11
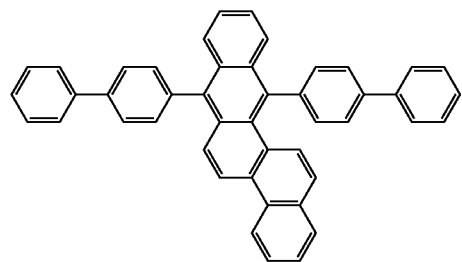
A12
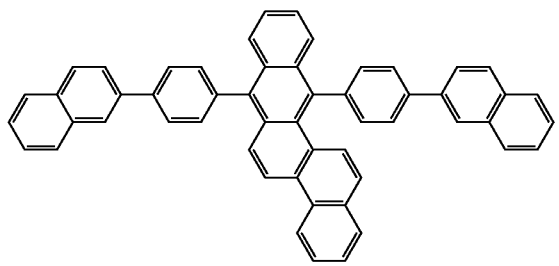
A13
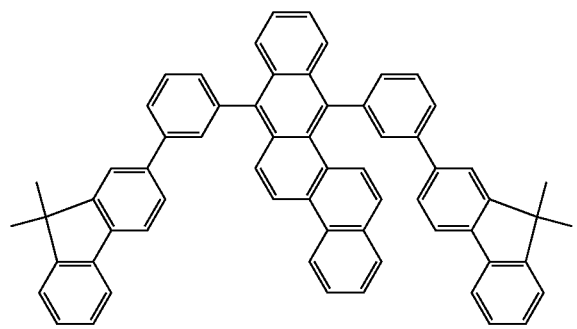
B01
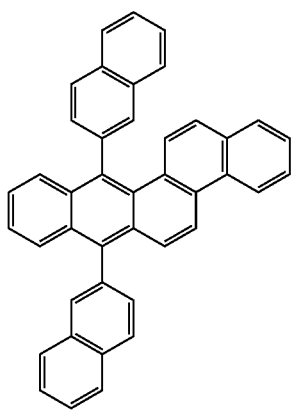
B02
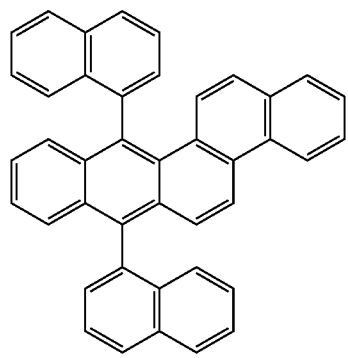
B03
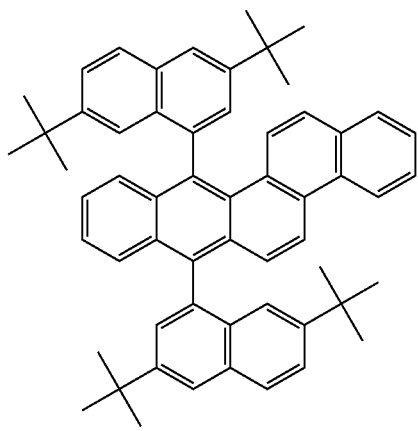

-continued
B04
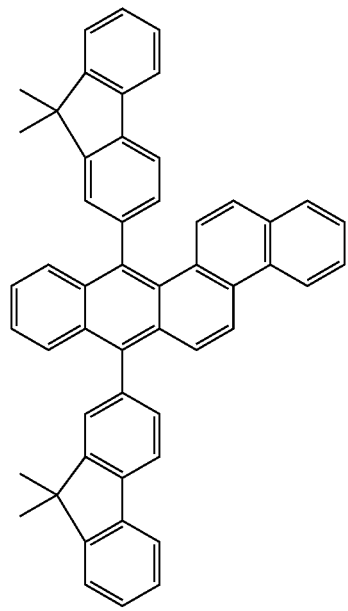
B05
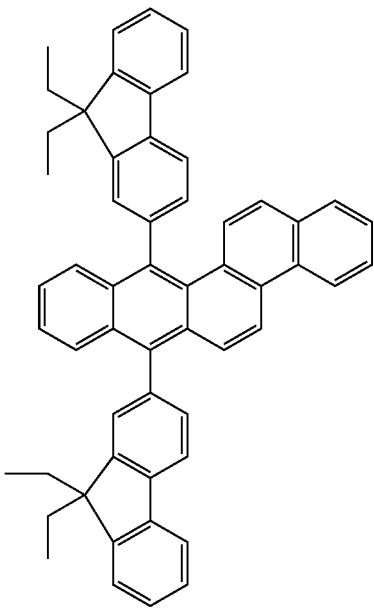
B06
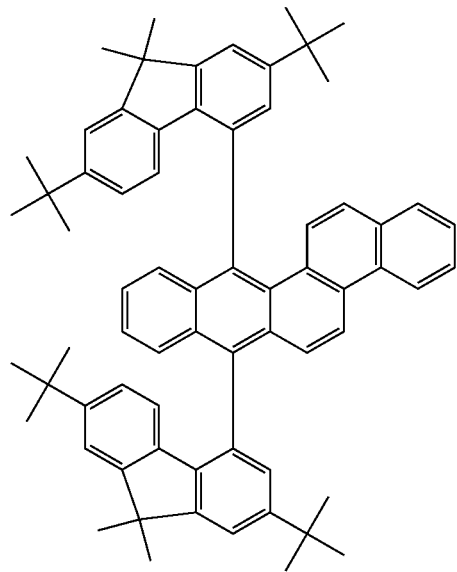
B07
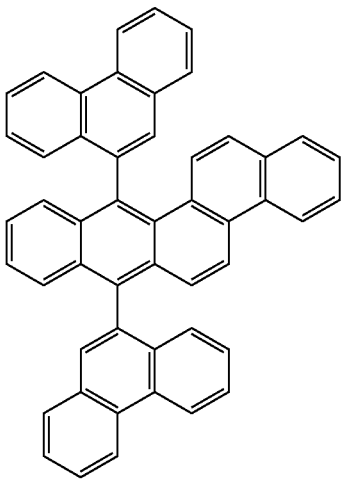

-continued
B08
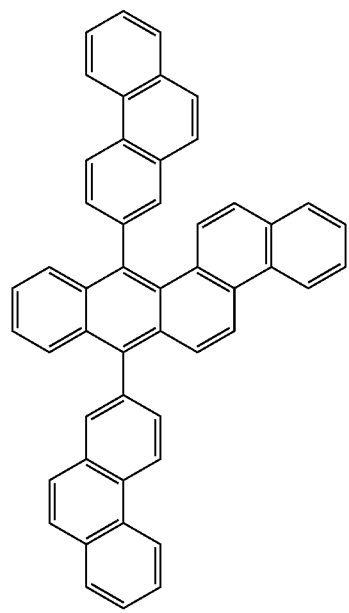
B09
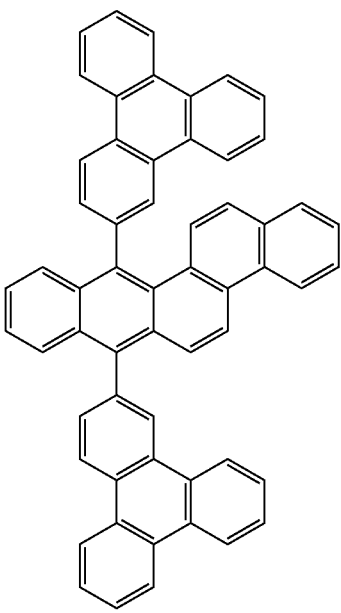
B10
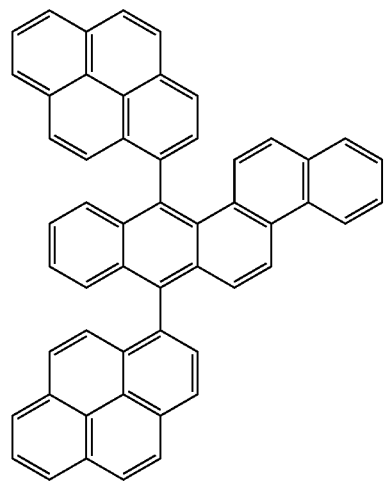
B11
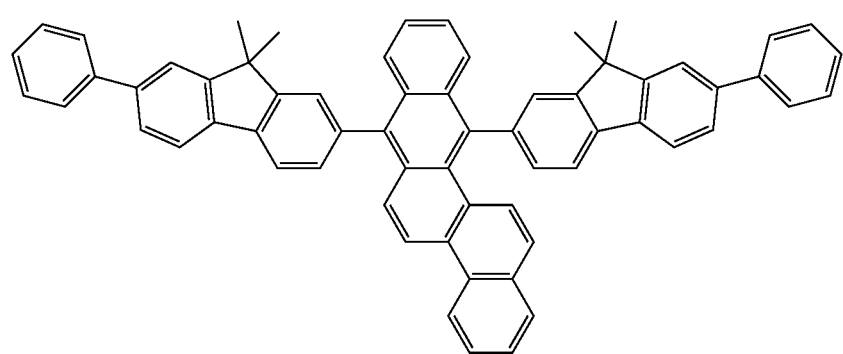

-continued
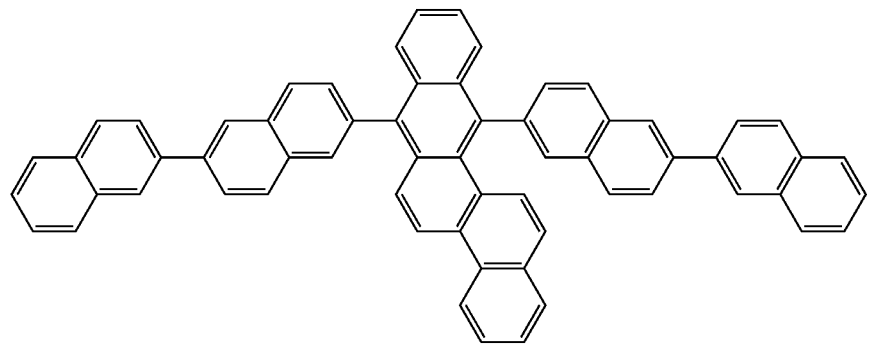
B12
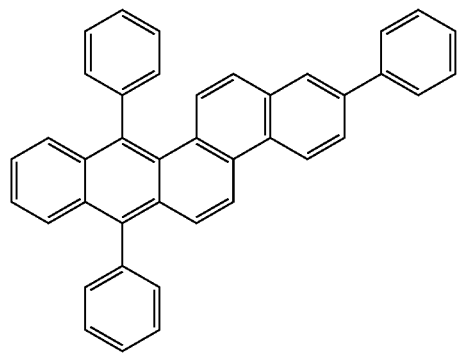
C01
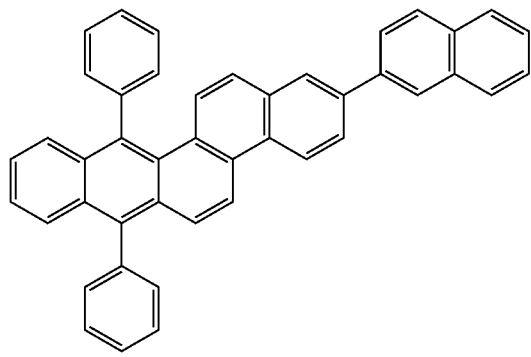
C02
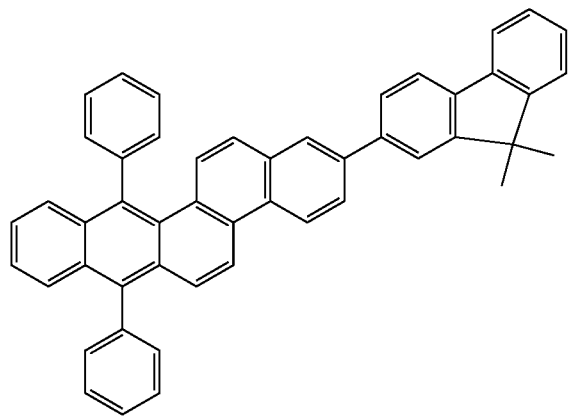
C03
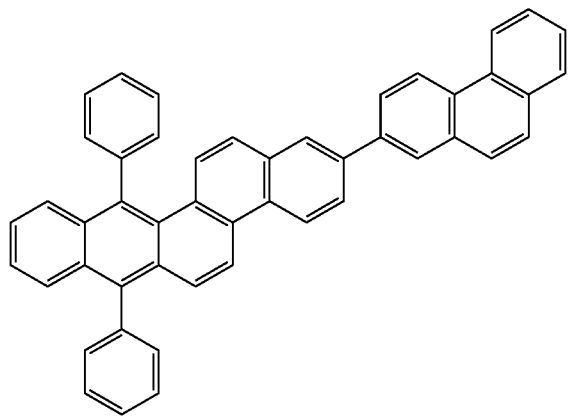
C04
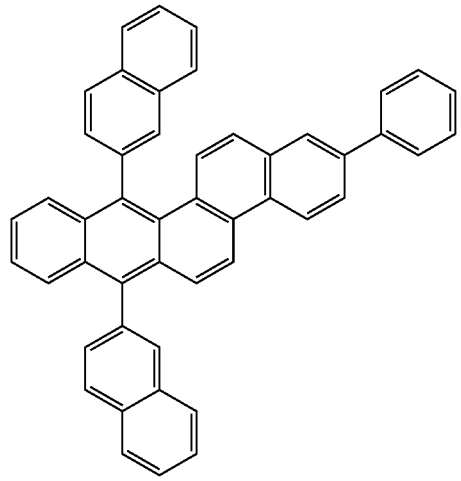
C05
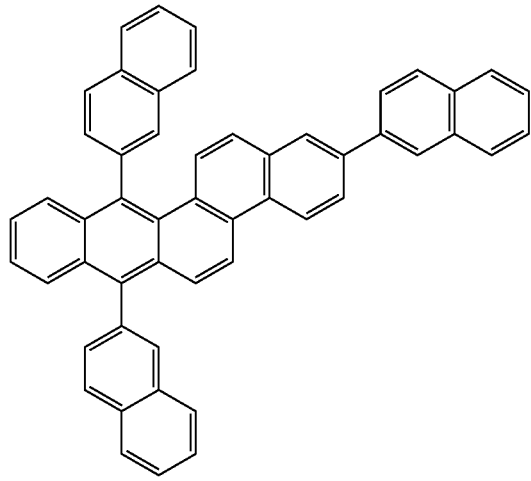
C06

-continued
C07
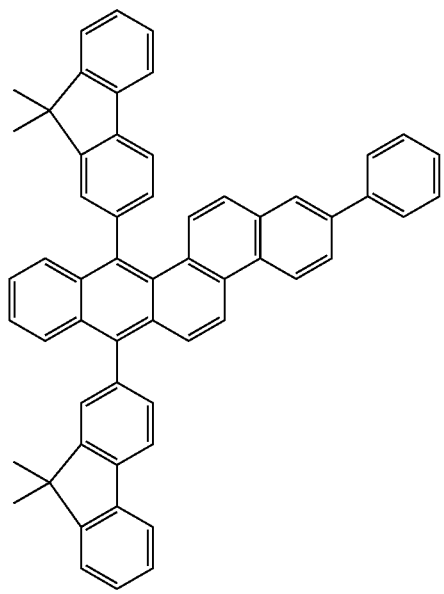
C08
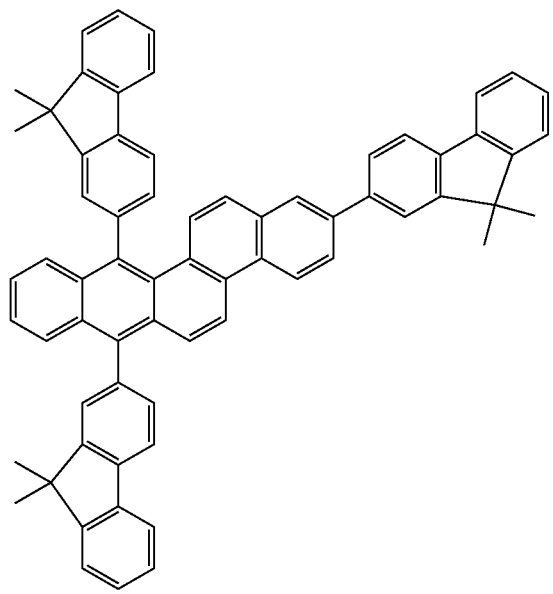
C09
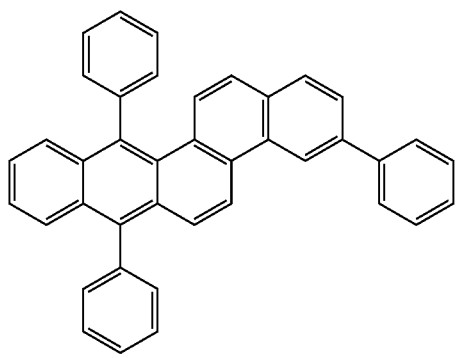
C10
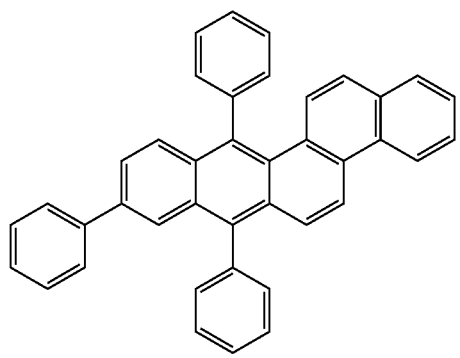
C11
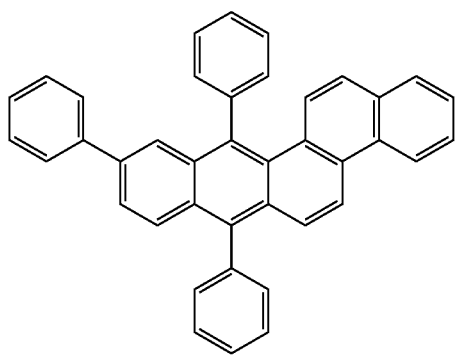
C12
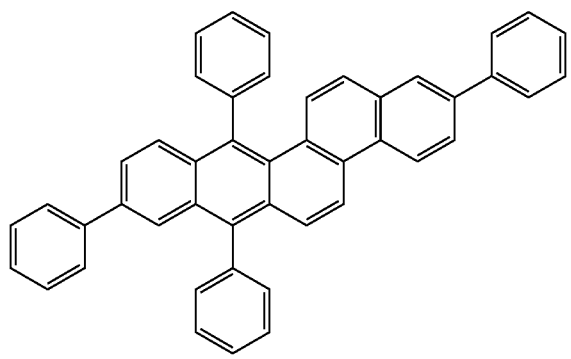

C13

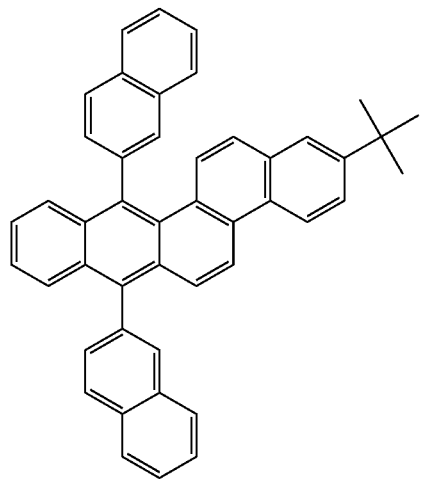

C14

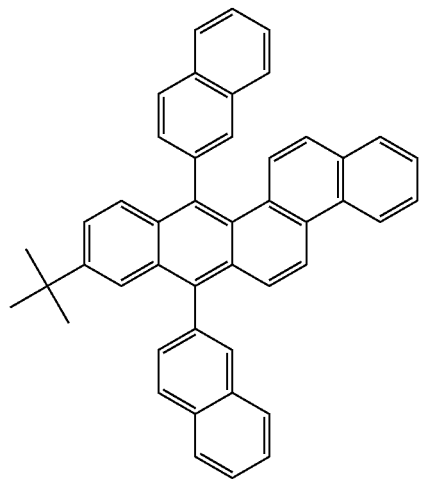

C15

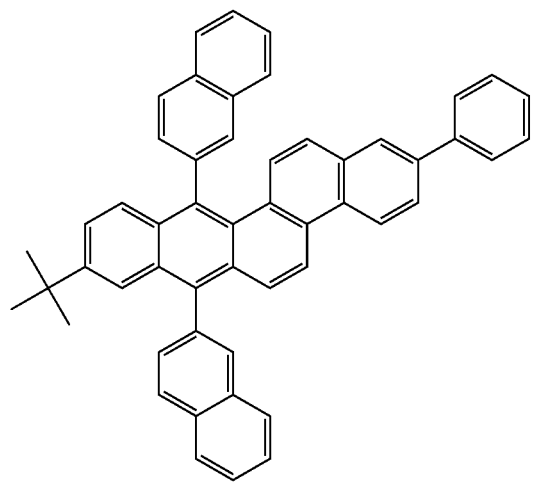

The compounds A01 to A13 (hereinafter, referred to as "set A") are compounds represented by general formula [3] in which the 7- and 12-positions of benzo[b]chrysene are substituted by substituted or unsubstituted phenyl groups. Therefore, the compounds in the set A are compounds having small extension of π conjugation due to substituted phenyl groups and thus having relatively high S1 energy among benzo[b]chrysene compounds according to aspects of the present invention.

Compound A01 is disclosed in Example 1, etc. described below. In the set A, compounds A03, A04, A05, and A07 have characteristics common to the compound A01. These can be generally represented by general formula [5] below.

[5]

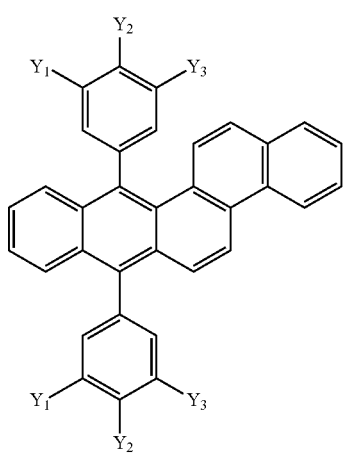

In the formula [5], Y1 to Y3 each independently represent a hydrogen atom or a substituted or unsubstituted alkyl group. Compounds represented by the formula [5] and the compound A01 have a common structure in that the α-positions of the substituted phenyl groups are not substituted. Therefore, these compounds have the property that the dihedral angle between the benzo[b]chrysene ring and each substituted phenyl group is equivalent to the compound A01, and thus the S1 energy is also equivalent to the compound A01.

Among the compounds represented by general formula [2], compounds B01 to B12 (hereinafter, referred to as "set B") are examples of compounds having, as Ar, a fused-ring aromatic hydrocarbon group other than a phenyl group. Therefore, the compounds in the set B are compounds having large extension of π conjugation due to the substituted fused ring group and thus having relatively low S1 energy among the benzo[b]chrysene compounds according to aspects of the present invention.

The compound B01 is disclosed in Example 2, etc. described below. In the set B, compounds B02, B04, B07, and B08 have characteristics common to the compound B01. These can be generally represented by general formula [6] below.

[6]

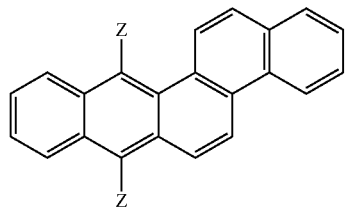

In the formula [6], Z represents any one of a 9,9-dimethylfluorenyl group and a phenanthryl group. Compounds represented by the formula [6] and the compound B01 have a common structure in that a substituent has substantially the same conjugate plane as a naphthyl group. Therefore, these compounds have the property that the extension of π conjugation from the benzo[b]chrysene ring to the substituent is equivalent to the compound B01, and thus the S1 energy is also equivalent to B01.

Among the compounds represented by the general formula [1], the compounds C01 to C15 (hereinafter, referred to as "set C") are examples of compounds having a substituent other than a hydrogen atom as at least one of $R_1$ to $R_4$. As described above, in the compounds in the set C which correspond to basic compounds in the sets A and B in which all the 1-, 2-, 9-, and 10-positions of benzo[b]chrysene are hydrogen atoms, the S1 energies and HOMO levels of the basic compounds are finely controlled. Specifically, compounds C09 to C12 each containing one or more phenyl substituents introduced to the basic compound A01 are compounds having lower S1 energies than that of the basic compound A01. In addition, compounds C13 and C14 each having an alkyl substituent introduced to the basic compound B01 have shallower HOMO levels than that of the basic compound B01.

(Organic Light-Emitting Element Including benzo[b]chrysene Compound According to Aspects of the Invention)

Next, an organic light-emitting element according to aspects of the present invention is described.

An organic light-emitting element according to aspects of the present invention includes a pair of electrodes and an organic compound layer disposed between the pair of electrodes. The organic compound layer essentially contains a benzo[b]chrysene compound represented by any one of the general formulae [1] to [3]. In addition, one or more layers other than the organic compound layer containing a benzo[b]chrysene compound according to aspects of the present invention may be provided between the pair of electrodes. The other layer may contain a benzo[b]chrysene compound according to aspects of the present invention. More specifically, the pair of electrodes includes an anode and a cathode, and the organic light-emitting element emits light when a voltage is applied between the pair of electrodes.

An example of the organic light-emitting element containing the benzo[b]chrysene compound according to aspects of the present invention is described below.

The organic light-emitting element according to aspects of the present invention may include a light emitting layer provided between the anode and the cathode as the pair of electrodes, may include a hole transport layer and a hole injection layer which are provided between the anode and the light emitting layer, or may include an electron transport layer, an electron injection layer, and a hole-exciton blocking layer which are provided between the light emitting layer and the cathode.

However, the configuration of the organic light-emitting element using the benzo[b]chrysene compound according to aspects of the present invention is not limited to this. For example, various layer structures may be used by providing an insulating layer at an interface between an electrode and the organic layer, providing an adhesive layer or an interference layer, providing an electron transport layer or hole transport layer which includes two layers with different ionization potentials, or providing a light emitting layer with a laminated structure including two or more layers.

Any one of the multiple layers disposed between the pair electrodes contains at least one of the benzo[b]chrysene compounds represented by the general formulae[1] to [3] according to aspects of the present invention. In this case, one of the layers may contain one or more of the benzo[b]chrysene compounds according to aspects of the present invention.

In the organic light-emitting element according to aspects of the present invention, the organic compound layer containing the benzo[b]chrysene compound according to aspects of the present invention may be a light emitting layer. Further, when the benzo[b]chrysene compound according to aspects of the present invention is used in the light emitting layer, the compound can be used as a host material of the light emitting layer.

In addition, the benzo[b]chrysene compound according to aspects of the present invention may be used as a guest material of the light emitting layer.

In addition, the benzo[b]chrysene compound according to aspects of the present invention may be used in each of the layers other than the light emitting layer, i.e., any one of the hole injection layer, the hole transport layer, the hole blocking layer, the exciton blocking layer, the electron transport layer, and the electron injection layer.

The light emitting layer may be composed of only the benzo[b]chrysene compound according to aspects of the present invention or partially composed of the benzo[b]chrysene compound according to aspects of the present invention. When the light emitting layer may be partially composed of the benzo[b]chrysene compound according to aspects of the present invention, the benzo[b]chrysene compound according to aspects of the present invention may be a main component or an accessory component.

The main component refers to a compound in a large amount by weight among all compounds constituting the light emitting layer, and the accessory component refers to a compound in a small amount. A material used as the main component can be referred to as a "host material". A material used as the accessory component can be referred to as a guest (dopant) material as described above, an emission assist material, or a charge injection material. Here, the guest material is a compound which contributes to main light emission in the light emitting layer. On the other hand, a host material is a compound which is present as a matrix around the guest material in the light emitting layer and which mainly contributes to carrier transport and donation of excitation energy to the guest material.

The concentration of the guest material for the host material is 0.01 wt % or more and 50 wt % or less, such as 0.1 wt % or more and 20 wt % or less, based on the total amount of the materials constituting the light emitting layer. In order to prevent concentration quenching, the concentration of the guest material may be 0.1 wt % or more and 10 wt % or less. In addition, the guest material may be contained uniformly over the entire layer including the host material or contained with a concentration gradient, or partially contained in a specified region to provide a host material layer not containing the guest material.

In order to enhance the luminous efficiency of the organic light-emitting element, it is important to increase the emission quantum yield of an emission central material serving as the guest material while enhancing the efficiency of excitation energy transfer between host and host or host and guest.

In order to achieve efficient excitation energy transfer between host and guest, it is necessary for the host material to have higher S1 energy than that of the guest material. That is, the S1 energy refers to an energy gap between the HOMO level and LUMO level of a compound.

However, when the S1 energy is excessively large, excitation energy transfer to the guest material is induced, but carrier injection to the light emitting layer from the adjacent hole transport layer or the electron transport layer is highly likely to be inhibited. This is because a hole injection barrier produced by a difference in HOMO level between the hole transport layer and the light emitting layer host and an electron injection barrier produced by a difference in LUMO level between the electron transport layer and the light emitting layer host are increased, thereby causing difficulty in injection of both carriers. Therefore, a higher bias voltage is required for injecting both carriers, leading to an increase in voltage of the organic light-emitting element, and balance between both carriers in the light emitting layer is greatly disrupted, leading to a decrease in luminous efficiency of the element.

In view of both the high-efficiency excitation energy transfer between host and guest and the good carrier injection, the inventors consider that there is a desired range of S1 energy of the host material according to the S1 energy of the guest material, i.e., luminescent color. For example, in a green fluorescent light-emitting element using a guest material which emits green light with the maximum emission wavelength of 490 nm to 520 nm, the inventors consider that the S1 energy of the host material may be about 2.8 eV, specifically 2.6 eV or more and 3.0 eV or less. The S1 energy may even be 2.7 eV or more and 2.9 eV or less.

Since the benzo[b]chrysene compound according to aspects of the present invention satisfies S1 energy within this numerical range, the compound can be used as a host material of a green light emitting layer.

Compounds known as a host material for a green fluorescent light-emitting element include an anthracene compound having an anthracene ring as a main skeleton and a chrysene compound having a chrysene ring as a main skeleton. However, the S1 energies of the anthracene compound and the chrysene compound are larger than the desired numerical range for the host material of the green fluorescent light-emitting element. On the other hand, as described above, the benzo[b]chrysene compound according to aspects of the present invention has smaller S1 energy than those of the anthracene compound and the chrysene compound and thus has S1 energy within the desired numerical range.

In this case, when the benzo[b]chrysene compound has excessively strong intermolecular stacking, S1 energy of a film form is decreased due to the formation of excimer and may be decreased to be lower than the desired numerical range. For example, unsubstituted benzo[b]chrysene has small S1 energy in a film form because of strong intermolecular stacking, and is thus difficult to use as a host material of the green fluorescent sublayer. However, as described above, intermolecular stacking of the benzo[b]chrysene compound according to aspects of the present invention is suppressed by the aromatic hydrocarbon substituents at the 7- and 12-positions, thereby preventing a decrease in the S1 energy.

Further, as described above, the benzo[b]chrysene compound according to aspects of the present invention has high oxidation resistance and high chemical stability due to the aromatic hydrocarbon substituents at the 7- and 12-positions, and thus little causes material deterioration with time, such as decomposition, due to element driving even when used for an organic light-emitting element. Therefore, the organic light-emitting element according to aspects of the present invention exhibits little deterioration in luminance and long life even when driven for a long time.

Further, as described above, the benzo[b]chrysene compound according to aspects of the present invention has a lower HOMO level than those of the anthracene compound and the chrysene compound. Therefore, when the benzo[b]chrysene compound according to aspects of the present invention is used as a host of the light emitting layer, a barrier to hole injection from the hole transport layer can be decreased. In this case, the drive voltage of the organic light-emitting element can be decreased, and an element with a high luminous efficiency can be produced.

Further, the benzo[b]chrysene compound according to aspects of the present invention is a compound having high carrier conductivity. Therefore, when the compound is used as a host of the light emitting layer, good carrier transport of holes and electrons can be made, and improvement in efficiency of the light-emitting element can be expected.

The benzo[b]chrysene compound according to aspects of the present invention may be used as a host material in a light emitting layer of a red light-emitting element or as a guest material in a light emitting layer of a blue light-emitting element.

Examples of a compound used as a guest material of an organic light-emitting element, more specifically a green light-emitting element, according to an embodiment of the present invention are given below.

[Green Luminescent Guest Material]

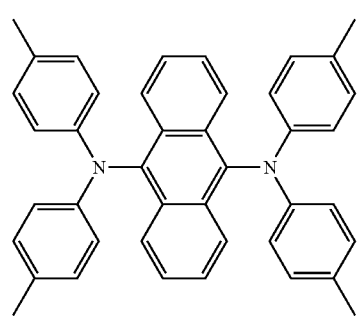

GD01

GD02
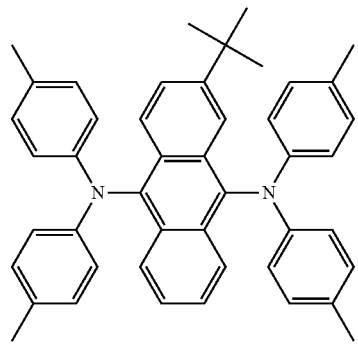

GD06
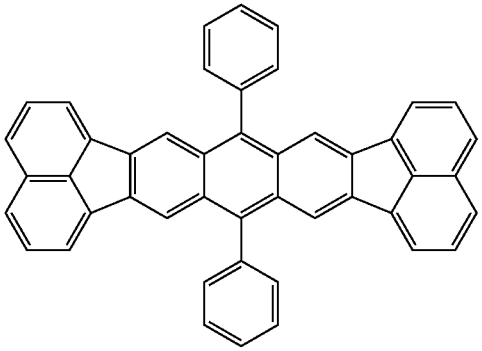

GD03
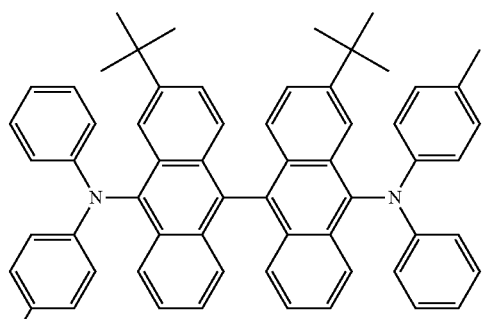

GD07
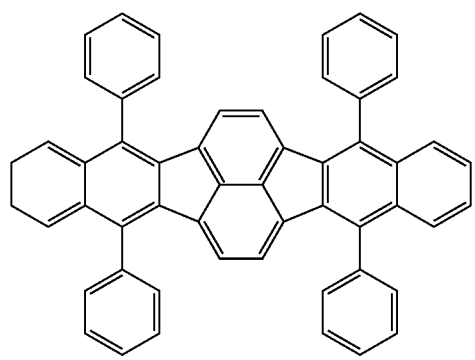

GD04
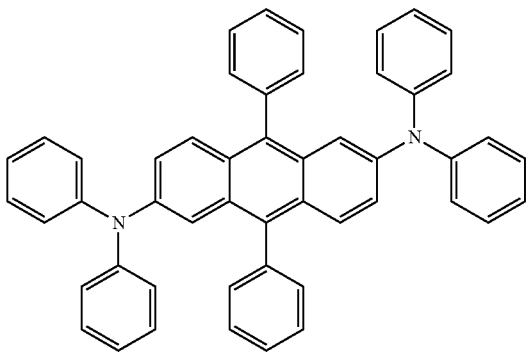

GD08
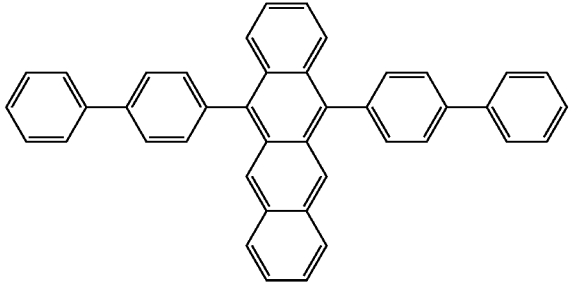

Besides the benzo[b]chrysene compound according to aspects of the present invention, the organic light-emitting element according to aspects of the present invention can use a known low-molecular or high-molecular hole transporting compound, a luminescent compound, or an electron transporting compound.

Examples of these compounds are given below.

A material with high hole mobility can be used as the hole injecting/transporting material. Examples thereof include triarylamine derivatives, phenylenediamine derivatives, stilbene derivatives, phthalocyanine derivatives, porphyrin derivatives, poly(vinylcarbazole), poly(thiophene), and other conductive polymers.

Besides the above-described green luminescent guest materials and derivatives thereof, examples of a luminescent material which is mainly involved in emission function include fused ring compounds (e.g., fluorene derivatives, naphthalene derivatives, pyrene derivatives, perylene derivatives, tetracene derivatives, anthracene derivatives, rubrene, and the like), quinacridone derivatives, coumarin derivatives, stilbene derivatives, organic aluminum complexes such as tris(8-quinolilate)aluminum and the like; organic beryllium complexes, and polymer derivatives such as poly(phenyle- GD05
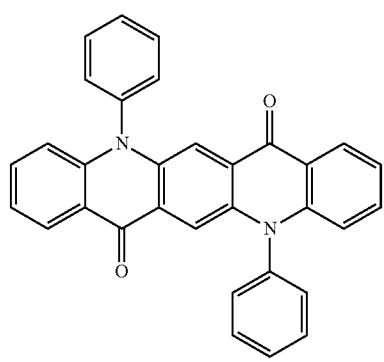

nevinylene) derivatives, poly(fluorene) derivatives, poly(phenylene) derivatives, and the like.

In view of balance with the hole mobility of the hole injecting/transporting material, the electron injecting/transporting material is selected. Examples of the electron injecting/transporting material include oxadiazole derivatives, oxazole derivatives, pyrazine derivatives, triazole derivatives, triazine derivatives, quinoline derivatives, quinoxaline derivatives, phenanthroline derivatives, organic aluminum complexes, and the like.

A material with as large a work function as possible can be used as an anode material. Examples of such a material include elemental metals such as gold, platinum, silver, copper, nickel, palladium, cobalt, selenium, vanadium, tungsten, and the like, alloys including combination thereof, metal oxides such as tin oxide, zinc oxide, indium oxide, indium tin oxide (ITO), indium zinc oxide, and the like. Also, conductive polymers such as polyaniline, polypyrrole, polythiophene, and the like can be used. These electrode materials can be used alone or in combination of two or more. In addition, the anode may be formed in a single layer or multiple layers.

On the other hand, a material with a small work function can be used as a cathode material. Examples of such a material include elemental metals such as alkali metals, e.g., lithium, alkaline-earth metals, e.g., calcium, aluminum, titanium, manganese, silver, lead, chromium, and the like. Also, alloys including combination of these elemental metals can be used. For example, magnesium-silver, aluminum-lithium, aluminum-magnesium, and the like can be used. Metal oxides such as indium tin oxide can also be used. These electrode materials can be used alone or in combination of two or more. In addition, the cathode may be formed in a single layer or multiple layers.

Any one of the anode and the cathode is transparent or semitransparent.

A substrate used in the organic light-emitting element according to this embodiment is not particularly limited, but a metal substrate, an opaque substrate such as a ceramic substrate, a transparent substrate composed of glass, quartz, a plastic sheet, or the like can be used. In addition, a color filter film, a fluorescent color conversion filter film, a dielectric reflection film, or the like can be used as the substrate in order to control a luminescent color.

In addition, for the purpose of preventing contact with oxygen, moisture, and the like, a protective layer or a sealing layer may be provided on the manufactured element. Examples of the protective layer include inorganic material films of diamond, metal oxides, metal nitrides, and the like; polymer films of fluorocarbon resins, polyethylene, silicone resins, polystyrene resins, and the like; and photocurable resin films. Further, the element can be coated with glass, a gas-impermeable film, a metal, or the like and packaged with a proper sealing resin.

With respect to the light emission direction of the element, any one of a bottom emission structure (light is emitted from the substrate side) and a top emission structure (light is emitted from the side opposite to the substrate) may be used.

In the organic light-emitting element according to aspects of the present invention, the layer containing the benzo[b]chrysene compound according to aspects of the present invention and the layer containing another organic compound are formed by the method described below. In general, a thin film is formed by a vacuum deposition method, an ionic vapor deposition method, sputtering, plasma, or a known coating method using a proper solvent solution (for example, spin coating, dipping, casting, LB, ink jet, or the like). The vacuum deposition method and the solution coating method are excellent in stability with time because crystallization and the like little occur. When a film is formed by the coating method, a film can be formed by combining an appropriate binder resin.

Examples of the binder resin include, but are not limited to, polyvinylcarbazole resins, polycarbonate resins, polyester resins, ABS resins, acryl resins, polyimide resins, phenol resins, epoxy resins, silicone resins, urea resins, and the like. These binder resins may be used as a homopolymer or a copolymer alone or as a mixture of two or more. Further, if required, known additives such as a plasticizer, an antioxidant, an ultraviolet absorber, and the like may be combined.

Examples of the organic light-emitting element according to aspects of the present invention include a display device, a latent image writing light source of an electrophotographic printer, a illuminating device, a backlight of a liquid crystal display device, an imaging unit of a digital camera, and the like.

A display device using the organic light-emitting element according to aspects of the present invention is described with reference to FIGURE. The display device includes the organic light-emitting element according to aspects of the present invention and a switching element which switches light emission of the organic light-emitting element.

First, reference numerals are described. Reference numeral 3 denotes the display device; reference numeral 31, a substrate, reference numeral 32, a moisture-proof layer; and reference numeral 33, a gate electrode. Reference numeral 34 denotes a gate insulating film; reference numeral 35, a semiconductor film, reference numeral 36, a drain electrode; reference numeral 37, a source electrode; reference numeral 38, a TFT element serving as the switching element; and reference numeral 39, an insulating film. In addition, reference numeral 310 denotes a contact hole (through hole); reference numeral 311, an anode, reference numeral 312, an organic layer; reference numeral 313, a cathode; reference numeral 314, a first protective layer; and reference numeral 315, a second protective layer.

FIGURE is a schematic sectional view showing the display device including the organic light-emitting element and TFT serving as the switching element connected to the organic light-emitting element. In this FIGURE, the display device includes two organic light-emitting elements. Each of the organic light-emitting elements is connected to the switching element.

The substrate 31 is composed of glass, and the moisture-proof film 32 is provided for protecting a member (e.g., the TFT or the organic layer) formed on the substrate.

Examples of a material constituting the moisture-proof film 32 include silicon oxide and a complex of silicon oxide and silicon nitride. Next, the gate electrode 33 is provided on the moisture-proof film 32. This is formed by forming a film of a metal such as Cr or the like by sputtering and patterning the resultant film in a predetermined circuit shape.

In addition, the gate insulating film 34 is provided on the gate electrode 33. The gate insulating film 34 is formed by forming a film of silicon oxide or the like by a plasma CVD method or a catalytic chemical vapor deposition method (cat-CVD method) and then patterning the film.

The semiconductor film 35 is provided corresponding to the gate electrode 33. The semiconductor film 35 is provided to cover the gate insulating film 34.

Further, the drain electrode 36 and the source electrode 37 are provided on the semiconductor film 35. The TFT element 38 includes the gate electrode, the gate insulating layer, the semiconductor layer, the source electrode, and the drain electrode, and the insulating film 39 is provided over the TFT element 38. The contact hole (through hole) 310 is provided in the insulating film 39 so that the organic light-emitting element anode 311 composed of a metal is connected to the source electrode 37, a conductive member being provided in the contact hole 310 in order to connect the anode 311 and the source electrode 37.

The multi- or single-layer organic layer 312 and the cathode 313 are laminated in order on the anode 311. In the drawing, the first protective layer 314 and the second protective layer 315 are provided for preventing degradation of the organic light-emitting element.

In the display device according to the embodiment of the present invention, the switching element is not particularly limited, and a single-crystal silicon substrate and a MIM element, an a-Si type, or the like can be used.

EXAMPLES

Aspects of the present invention are described in detail below with reference to examples. However, the present invention is not limited to these examples.

Example 1

Synthesis of Exemplified Compound A01

(1) Synthesis of Intermediate ANCl-1

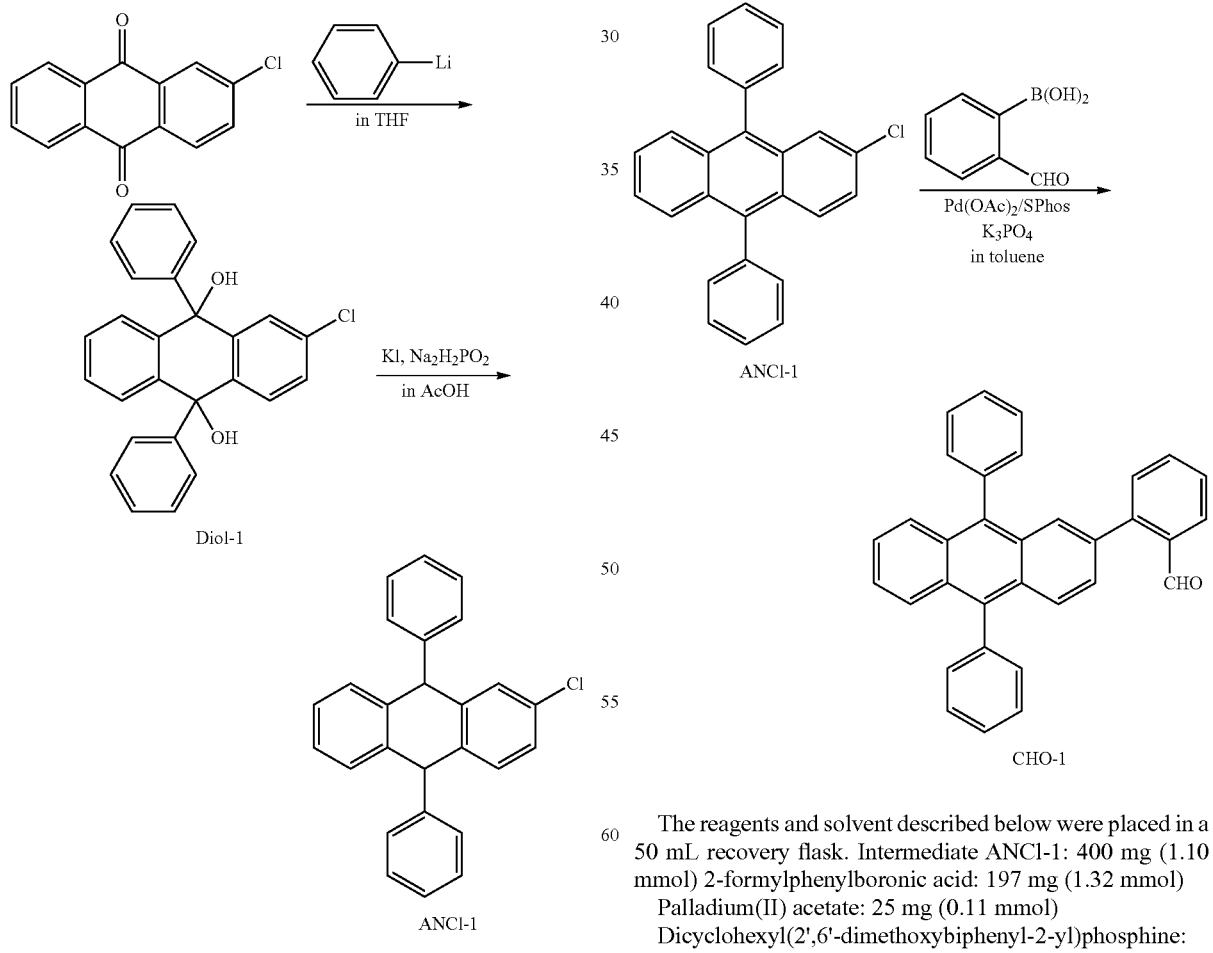

In a 100 mL three-necked flask purged with nitrogen, 34 mL of dehydrated THF was charged and cooled, 28.6 mL (30.9 mmol) of a 1.08 M cyclohexane/diethyl ether solution of phenyl lithium was added at −78° C., and then 3.00 g (12.4 mmol) of 2-chloroanthraquinone was slowly added. After the completion of addition, the resultant mixture was stirred at room temperature for 7 hours, and a saturated aqueous ammonium chloride solution was added to terminate reaction. Then, the product was extracted from the reaction solution with dichloromethane, washed twice with water, dried over sodium sulfate, and then concentrated to produce a crude product. Then, the crude product was washed with a heptane/chloroform mixed solvent to produce 4.27 g of intermediate Diol-1 (yield 86%).

Then, the raw materials, reagent, and solvent described below were placed in a 300 mL recovery flask.
Intermediate Diol-1: 4.26 g (10.7 mmol)
Potassium iodide: 16.5 g (99.4 mmol)
$NaH_2PO_2.H_2O$: 18.7 g (176 mmol) Acetic acid: 160 mL The reaction solution was heated under reflux with stirring for 3 hours. After the completion of reaction, the reaction solution was cooled to room temperature, water was added to the reaction solution, and precipitate was filtered off to produce a pale yellow powder of a crude product. Then, the crude product was washed with a methanol/ethanol mixed solvent to produce 3.80 g of intermediate ANCl-1 (yield 97%).

(2) Synthesis of Intermediate CHO-1

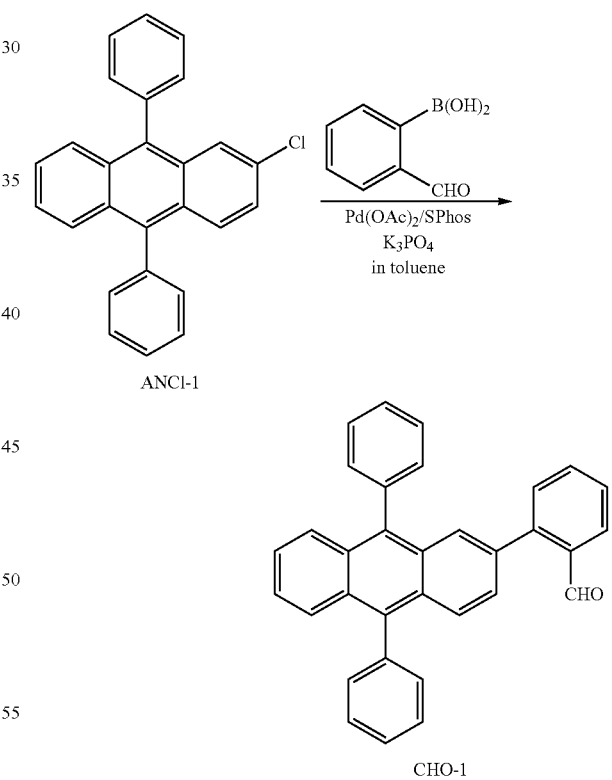

The reagents and solvent described below were placed in a 50 mL recovery flask. Intermediate ANCl-1: 400 mg (1.10 mmol) 2-formylphenylboronic acid: 197 mg (1.32 mmol)
Palladium(II) acetate: 25 mg (0.11 mmol)
Dicyclohexyl(2',6'-dimethoxybiphenyl-2-yl)phosphine: 113 mg (0.27 mmol)
Potassium phosphate: 700 mg (3.29 mmol)
Toluene: 20 mL The reaction solution was heated to 100° C. under nitrogen and subjected to reaction with stirring for 15 hours. After the completion of reaction, the reaction solution was washed with water, dried over sodium sulfate, and then concentrated to produce a crude product. Then, the crude product was purified by silica gel column chromatography (eluent heptane/chloroform=2/1) to produce 394 mg of intermediate CHO-1 (yield 83%).

(3) Synthesis of Exemplified Compound A01

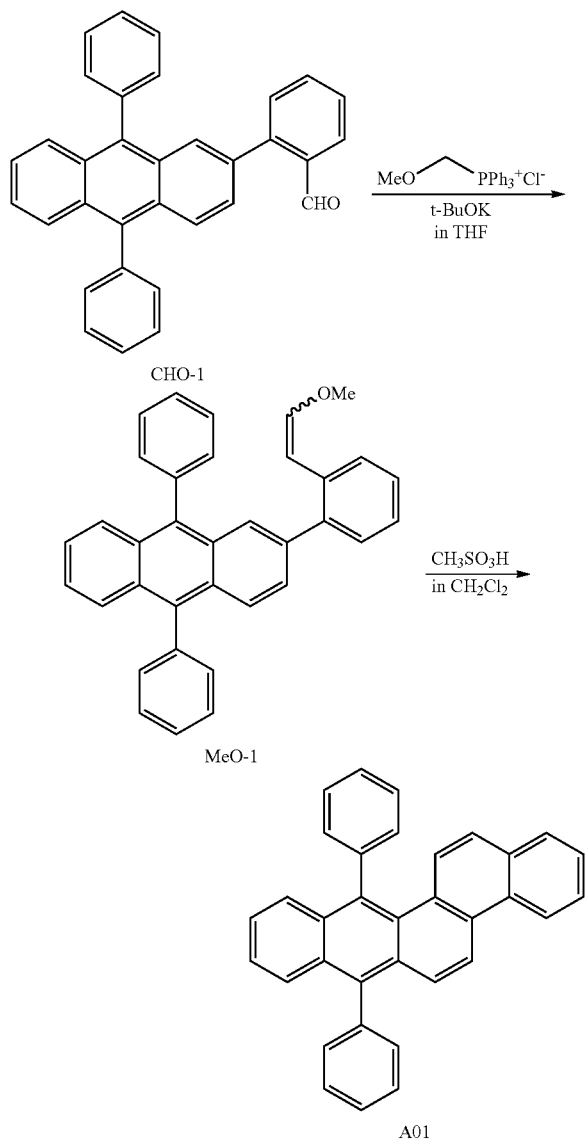

In a 50 mL recovery flask purged with nitrogen, 777 mg (2.27 mmol) of (methoxymethyl)triphenylphosphonium chloride and 3.9 mL of dehydrated diethyl ether were charged and stirred, and then 2.27 mL (2.27 mmol) of a 1M THF solution of potassium tert-butoxide was added, followed by stirring for 1 hour. Then, a solution prepared by dissolving 394 mg (0.91 mmol) of intermediate CHO-1 in 9.5 mL of THF solvent was added to the reaction solution and further stirred at room temperature for 4 hours, and then water was added to the reaction solution to terminate reaction. Then, an aqueous phase was extracted with ethyl acetate three times by a separating operation, and the organic phase was washed with water, dried over sodium sulfate, and then concentrated to produce a crude product. Then, the crude product was purified by silica gel column chromatography (eluent: heptane/toluene=3/1) to produce 304 mg of intermediate MeO-1 (yield 73%).

Then, in a 10 mL recovery flask purged with nitrogen, 304 mg (0.66 mmol) of intermediate MeO-1 and 3.7 mL of dehydrated dichloromethane were added and stirred, and one drop of methanesulfonic acid was added with a Pasteur pipette and stirred at room temperature for 3 hours, and then methanol was added to terminate reaction. The produced yellow precipitate was filtered off, purified by silica gel column chromatography (eluent: heptane/toluene=4/1), and recrystallized from an octane/toluene mixed solvent. The resultant yellow crystals were dried at 120° C. under vacuum and purified by sublimation at $10^{-4}$ Pa and 280° C. to produce 96 mg of high-purity exemplified compound A01 (yield 34%).

The results of identification of the resultant compound are shown below.

[MALDI-TOF-MS (matrix-assisted laser desorption ionization-time-of-flight mass spectrometry)

Measured value: m/z=430.22

Calculated value: $C_{34}H_{22}$=430.17 [$^1$H-NMR (400 MHz, Cl$_3$)] δ 8.65 (d, 1H), 8.46 (d, 1H), 7.94-7.68 (m, 5H), 7.68-7.47 (m, 12H), 7.47-7.36 (m, 3H)

Also, the S1 energy of Exemplified Compound A01 was measured by the following method. Exemplified Compound A01 was deposited on a glass substrate by heating to form an evaporated thin film of 20 nm in thickness. An absorption spectrum of the deposited thin film was measured with an ultraviolet visible spectrophotometer (V-560 manufactured by JASCO Corporation). As a result of determination of the absorption edge of the obtained absorption spectrum, the absorption edge was 437 nm, and the S1 energy of Exemplified Compound A01 was 2.84 eV.

Further, the ionization potential of Exemplified Compound A01 was measured by the following method. The ionization potential was measured with photoelectron spectrometer AC-2 (manufactured by Riken Keiki Co., Ltd.) using the deposited thin film used for measuring the S1 energy. As a result of the measurement, the ionization potential of Exemplified Compound A01 was 5.70 eV.

Example 2

Synthesis of Exemplified Compound B01

(1) Synthesis of Intermediate ANCl-2

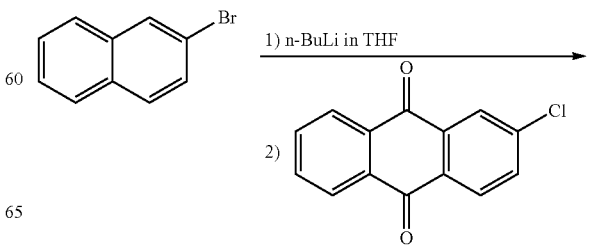

(2) Synthesis of Intermediate CHO-2

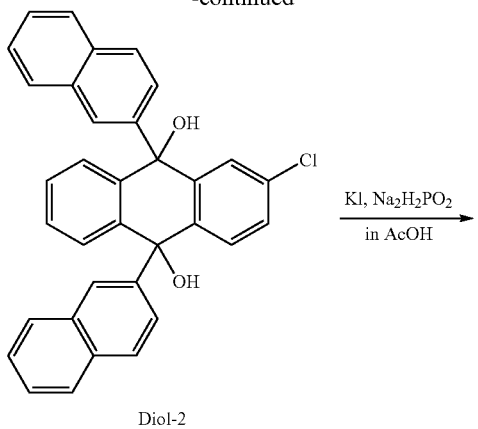

Diol-2

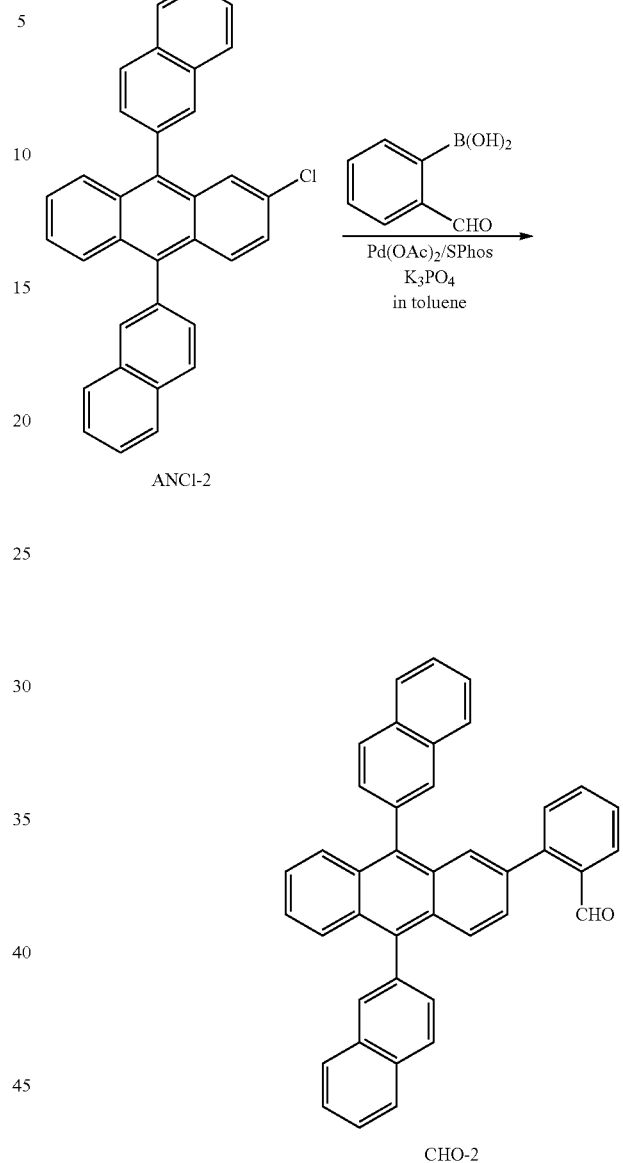

ANCl-2

CHO-2

In a 200 mL three-necked flask purged with nitrogen, 8.53 g (41.2 mmol) of 2-bromonaphthalene and 57 mL of dehydrated THF were added and cooled to −78° C., and 25.8 mL (41.2 mmol) of a 1.6 M hexane solution of n-butyllithium was added dropwise to the resultant mixture. After the completion of addition, the resultant mixture was slowly heated to −20° C., and then 4.00 g (16.5 mmol) of 2-chloroanthraquinone was added slowly. After the completion of addition, the mixture was stirred at room temperature over night, and a saturated aqueous ammonium chloride solution was added to terminate reaction. Then, the product was extracted from the reaction solution with dichloromethane, washed twice with water, dried over sodium sulfate, and then concentrated to produce a crude product. Then, the crude product was washed with a heptane/chloroform mixed solvent to produce 6.75 g of intermediate Diol-2 (yield 82%).

Then, the raw materials, reagent, and solvent described below were placed in a 500 mL recovery flask.

Intermediate Diol-2: 6.68 g (13.4 mmol) Potassium iodide: 20.7 g (124 mmol)

$NaH_2PO_2 \cdot H_2O$: 23.4 g (221 mmol) Acetic acid: 250 mL

The reaction solution was heated under reflux with stirring for 3.5 hours. After the completion of reaction, the reaction solution was cooled to room temperature, water was added to the reaction solution, and the precipitate was filtered off to produce a yellow powder of a crude product. Then, the crude product was washed with a methanol solvent to produce 5.68 g of intermediate ANCl-2 (yield 91%).

The reagents and solvent described below were placed in a 100 mL recovery flask.

Intermediate ANCl-2: 1.00 g (2.15 mmol)
2-formylphenylboronic acid: 387 mg (2.58 mmol)
Palladium(II) acetate: 48 mg (0.11 mmol)
Dicyclohexyl(2',6'-dimethoxybiphenyl-2-yl)phosphine: 221 mg (0.54 mmol)
Potassium phosphate: 1.37 mg (6.45 mmol)
Toluene: 40 mL The reaction solution was heated to 100° C. under nitrogen and subjected to reaction with stirring for 10 hours. After the completion of reaction, the reaction solution was washed with water, dried over sodium sulfate, and then concentrated to produce a crude product. Then, the crude product was purified by silica gel column chromatography (eluent: heptane/toluene=1/1) to produce 1.12 g of intermediate CHO-2 (yield 98%).

(3) Synthesis of Exemplified Compound B01

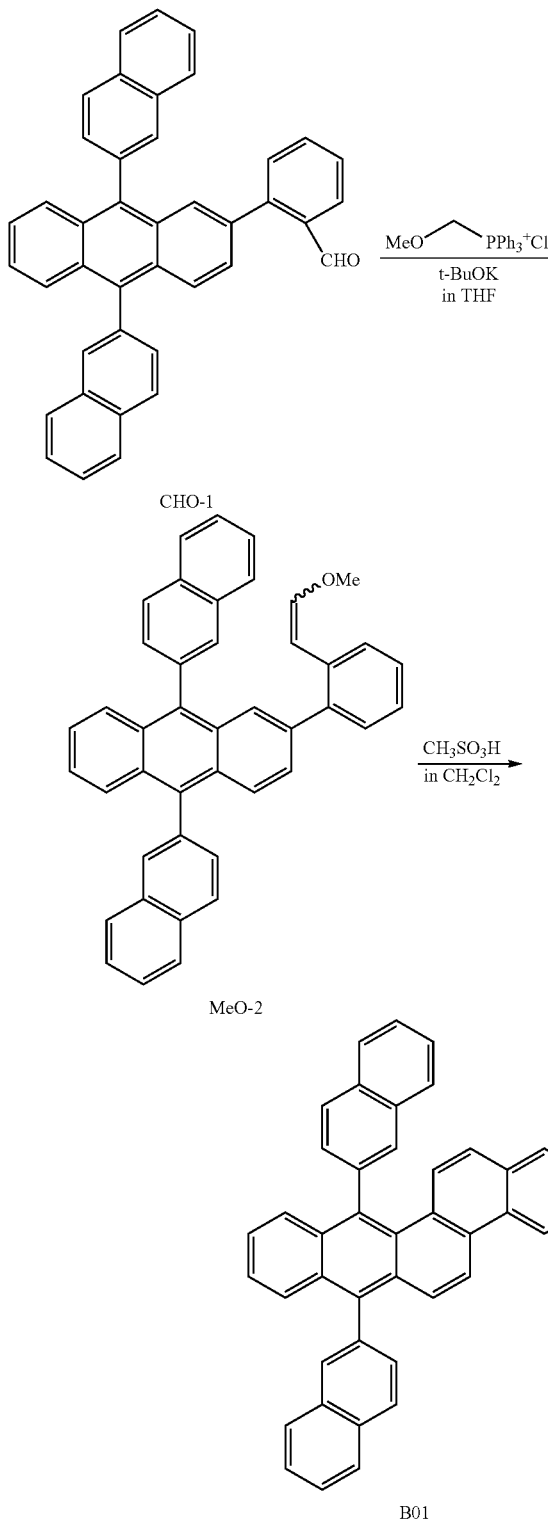

In a 200 mL recovery flask purged with nitrogen, 1.80 g (5.25 mmol) of (methoxymethyl)triphenylphosphonium chloride and 9 mL of dehydrated diethyl ether were charged and stirred, and then 5.25 mL (5.25 mmol) of a 1M THF solution of potassium tert-butoxide was added, followed by stirring for 1 hour. Then, a solution prepared by dissolving 1.12 g (2.09 mmol) of intermediate CHO-2 in 25 mL of THF solvent was added to the reaction solution and further stirred at room temperature for 3.5 hours, and then water was added to the reaction solution to terminate reaction. Then, an aqueous phase was extracted with ethyl acetate three times by a separating operation, and an organic phase was washed with water, dried over sodium sulfate, and then concentrated to produce a crude product. Then, the crude product was purified by silica gel column chromatography (eluent: heptane/toluene=3/1) to produce 1.10 g of intermediate MeO-2 (yield 93%).

Then, in a 100 mL recovery flask purged with nitrogen, 1.03 g (1.83 mmol) of intermediate MeO-2 and mL of dehydrated dichloromethane were added and stirred, and three drops of methanesulfonic acid were added with a Pasteur pipette and stirred at room temperature for 2 hours, and then methanol was added to terminate reaction. The produced yellow precipitate was filtered off, purified by silica gel column chromatography (eluent: heptane/toluene=4/1), and recrystallized with an octane/toluene mixed solvent. The resultant yellow crystals were dried at 150° C. under vacuum and then purified by sublimation at $10^{-4}$ Pa and 300° C. to produce 293 mg of high-purity exemplified compound B01 (yield 30%).

The results of identification of the resultant compound are shown below.

[MALDI-TOF-MS]

Measured value: m/z=530.27 Calculated value: $C_{42}H_{26}$=530.20 [$^1$H-NMR (400 MHz, CDCl$_3$)] δ8.64 (d, 1H), 8.45 (d, 1H), 8.20-8.00 (m, 5H), 8.00-7.90 (m, 12H), 7.90-7.50 (m, 15H), 7.45-7.33 (m, 2H)

Also, as a result of measurement of the S1 energy of Exemplified Compound B01 by the same method as in Example 1-(3), the absorption end of the absorption spectrum was 446 nm, and the S1 energy of Exemplified Compound B01 was 2.78 eV.

Further, as a result of measurement of the ionization potential of Exemplified Compound B01 by the same method as in Example 1-(3), the ionization potential of Exemplified Compound B01 was 5.79 eV.

Comparative Example 1

Comparison of S1 Energy and Ionization Potential

The S1 energies and ionization potentials of Comparative Compounds GH01 to GH03 described below were measured by the same method as in Example 1-(3). The results are shown in Table 2 together with the results of Examples 1 and 2.

[Comparative Compound]

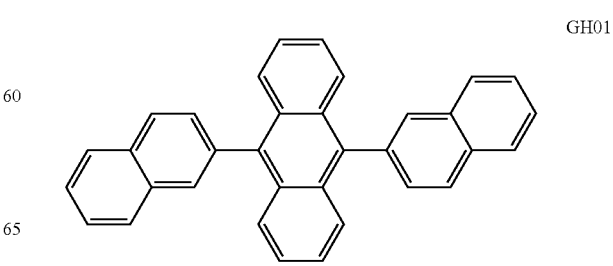

GH01

-continued

GH02

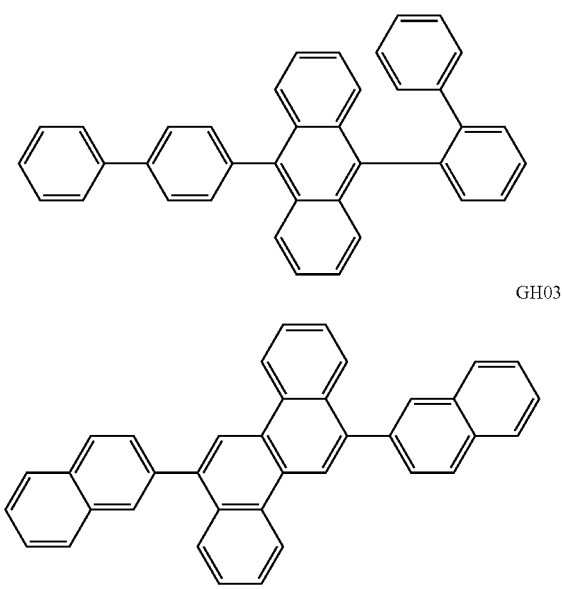

GH03

TABLE 2

| | Absorption end | S1 energy |
|---|---|---|
| Exemplified Compound A01 | 437 nm | 2.84 eV |
| Exemplified Compound B01 | 446 nm | 2.78 eV |
| Comparative Compound GH01 | 426 nm | 2.91 eV |
| Comparative Compound GH02 | 425 nm | 2.92 eV |
| Comparative Compound GH03 | 395 nm | 3.14 eV |

Comparative Compounds GH01 to GH03 which are an anthracene compound and a chrysene compound have a S1 energy of as large as 2.9 eV or more, an ionization potential of as high as about 5.9 eV, and a deep HOMO level as compared with the benzo[b]chrysene compounds of the examples according to aspects of the present invention.

Example 3

In this example, an organic light-emitting element was formed by a method described below to have a configuration in which an anode, a hole transport layer, a light emitting layer, an electron transport layer, and a cathode were provided in order on a substrate, the electron transport layer including two layers having different ionization potentials.

A glass substrate on which ITO was deposited by sputtering to form a film as the anode having a thickness of 120 nm was used as a transparent conductive support substrate (ITO substrate). hen, organic compound layers and electrode layers described below were continuously formed on the ITO substrate by resistance-heating vacuum deposition in a vacuum chamber of $10^{-5}$ Pa. In this case, the opposing electrode layers were formed to have an electrode area of 3 mm². Hole transport layer (40 nm) HTL-1 light emitting layer (30 nm) Host material: Exemplified Compound A01 Guest material: GD-7 (ratio by weight 2%)

Electron transport layer 1 (10 nm) ETL-1
Electron transport layer 2 (30 nm) ETL-2
Metal electrode layer 1 (0.5 nm) LiF
Metal electrode layer 2 (100 nm) Al

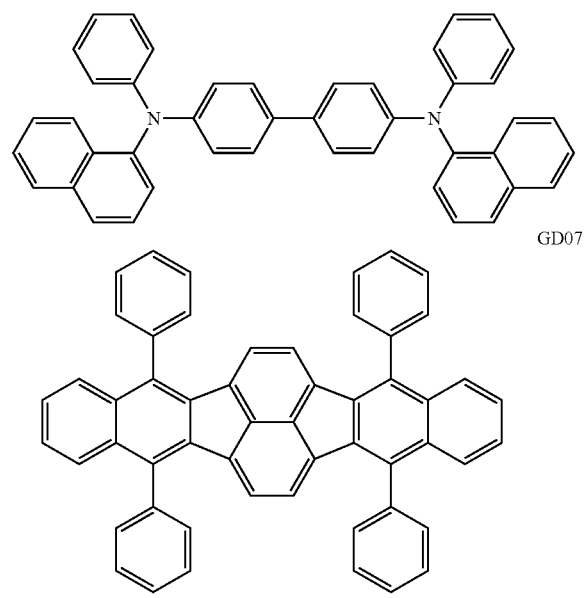

HTL-1

GD07

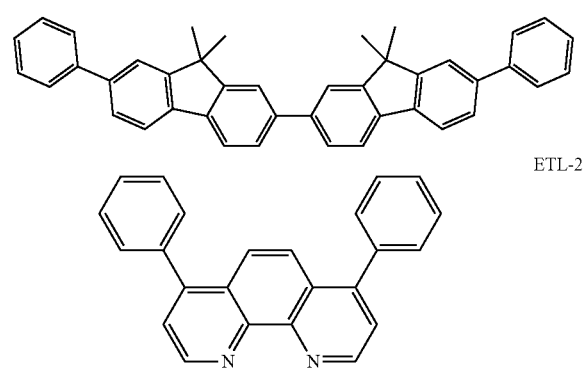

ETL-1

ETL-2

Next, in order to prevent degradation of the organic light-emitting element due to water adsorption, the element was covered with a protective glass plate in a dry air atmosphere and sealed with an acryl resin adhesive. The organic light-emitting element was formed as described above.

When a voltage of 5.0 V was applied to the resultant organic light-emitting element using the ITO electrode as an anode and the Al electrode as a cathode, green light emission with a luminous efficiency of 13.8 cd/A and a luminance of 2000 cd/m² was observed. In addition, the CIE chromaticity coordinates of the element were (x, y)=(0.29, 0.64). Further, as a result of duration driving of the element for 100 hours while maintaining a constant-current density of 100 mA/cm², a decrease in luminance from the initial value was 12%.

Example 4

An element was formed by the same method as in Example 3 except that Exemplified Compound B01 was used in place of Exemplified Compound A01 as a host material of a light emitting layer. In addition, the resultant element was evaluated by the same method as in Example 3. The results are shown in Table 3.

Comparative Example 2

An element was formed by the same method as in Example 3 except that Comparative Compound GH01 was used in place of Exemplified Compound A01 as a host material of a light emitting layer. In addition, the resultant element was evaluated by the same method as in Example 3.
The results are shown in Table 3.

Comparative Example 3

An element was formed by the same method as in Example 3 except that Comparative Compound GH02 was used in place of Exemplified Compound A01 as a host material of a light emitting layer.
In addition, the resultant element was evaluated by the same method as in Example 3. The results are shown in Table 3.

Comparative Example 4

An element was formed by the same method as in Example 3 except that Comparative Compound GH03 was used in place of Exemplified Compound A01 as a host material of a light emitting layer. In addition, the resultant element was evaluated by the same method as in Example 3. The results are shown in Table 3.

TABLE 3

| | Light emitting layer host material | CIE chromaticity | Applied voltage @2000 cd/m² (V) | Luminous efficiency @2000 cd/m² (cd/A) | Rate of decrease in luminance 100 hours after @2000 cd/m² (cd/A) |
|---|---|---|---|---|---|
| Example 3 | Exemplified Compound A01 | (0.29, 0.64) | 5.0 | 13.8 | 12% |
| Example 4 | Exemplified Compound B01 | (0.30, 0.63) | 5.1 | 15.0 | 20% |
| Comparative Example 2 | Comparative Compound GH01 | (0.30, 0.64) | 6.1 | 10.4 | 39% |
| Comparative Example 3 | Comparative Compound GH02 | (0.30, 0.64) | 6.0 | 11.0 | 36% |
| Comparative Example 4 | Comparative Compound GH03 | (0.29, 0.64) | 6.7 | 9.5 | 51% |

As described above, an organic light-emitting element using the benzo[b]chrysene compound according to aspects of the present invention as a host material of a light emitting layer can exhibit light emission with a luminance of 2000 cd/m² and a high luminous efficiency of 12 cd/A or more at a low applied voltage of less than 6 V. As described above in the embodiments and examples, according to aspects of the present invention, a novel benzo[b]chrysene compound can be provided. In addition, an organic light-emitting element using the benzo[b]chrysene compound and exhibiting high luminous efficiency and a low drive voltage can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-082816, filed Mar. 31, 2010 which is hereby incorporated by reference herein in its entirety.

What is claimed is:

1. A benzo[b]chrysene compound represented by the following general formula [1]:

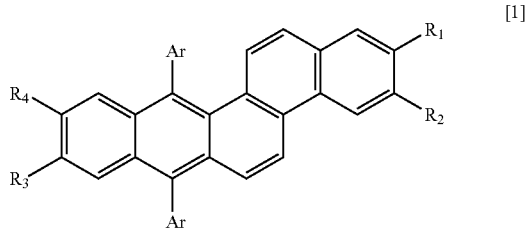

[1]

wherein in the general formula [1], Ar represents a substituted or unsubstituted aromatic hydrocarbon group, and $R_1$ to $R_4$ are each independently selected from the group consisting of a hydrogen atom, substituted or unsubstituted alkyl groups, and substituted or unsubstituted aromatic hydrocarbon groups.

2. The benzo[b]chrysene compound according to claim 1, represented by the following general formula [2]:

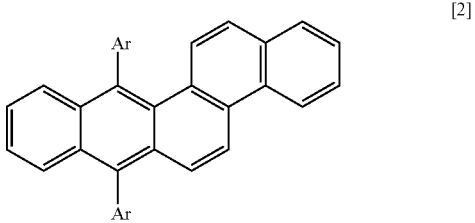

[2]

wherein in the general formula [2], Ar represents the substituted or unsubstituted aromatic hydrocarbon group.

3. The benzo[b]chrysene compound according to claim 2, represented by the following general formula [3]:

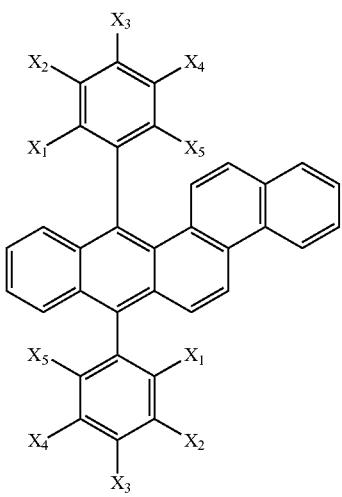

[3]

wherein in the general formula [3], $X_1$ to $X_5$ are each independently selected from the group consisting of a hydrogen atom, substituted or unsubstituted alkyl groups, and substituted or unsubstituted aromatic hydrocarbon groups.

4. An organic light-emitting element comprising:

a pair of electrodes; and an organic compound layer disposed between the pair of electrodes, wherein the organic compound layer contains the benzo[b]chrysene compound according to claim 1.

5. The organic light-emitting element according to claim 4, wherein the organic compound layer is a light emitting layer containing a host material and a guest material, and the host material is the benzo[b]chrysene compound according to claim 1.

6. A display device comprising:

the organic light-emitting element according to claim 4; and a switching element connected to the organic light-emitting element.

7. The organic light-emitting element according to claim 5, wherein the guest is at least one of the following compounds:

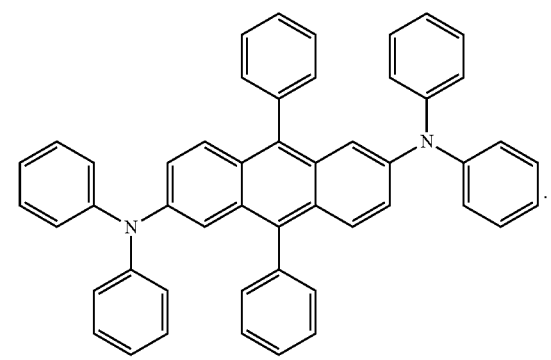

8. The organic light-emitting element according to claim 5, wherein the guest is an anthracene derivative.

9. The organic light-emitting element according to claim 5, wherein the guest is at least one of the following compounds:

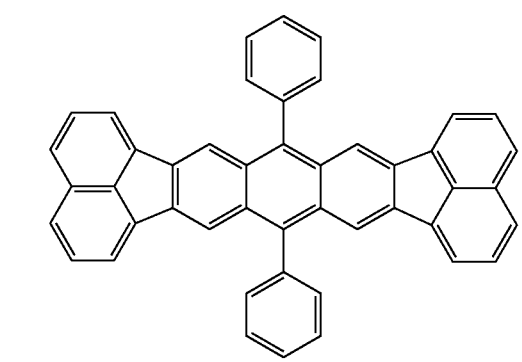

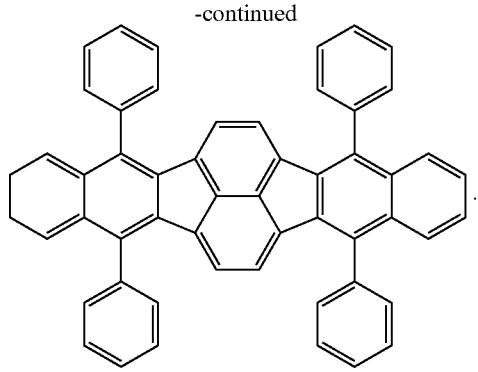
10. A device comprising the organic light-emitting element according to claim 5 and a color filter.
11. An illuminating device comprising the organic light-emitting element according to claim 5.
12. An electrophotographic printer comprising a latent image writing light source having the organic light-emitting element according to claim 5.
* * * * *